US011636919B2

(12) United States Patent
Hubbell et al.

(10) Patent No.: US 11,636,919 B2
(45) Date of Patent: Apr. 25, 2023

(54) METHODS, SYSTEMS, AND COMPUTER READABLE MEDIA FOR EVALUATING VARIANT LIKELIHOOD

(71) Applicant: LIFE TECHNOLOGIES CORPORATION, Carlsbad, CA (US)

(72) Inventors: Earl Hubbell, Palo Alto, CA (US); Sowmi Utiramerur, Cupertino, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 1357 days.

(21) Appl. No.: 15/974,976

(22) Filed: May 9, 2018

(65) Prior Publication Data
US 2018/0330051 A1 Nov. 15, 2018

Related U.S. Application Data

(63) Continuation of application No. 14/200,942, filed on Mar. 7, 2014, now abandoned.

(60) Provisional application No. 61/782,240, filed on Mar. 14, 2013.

(51) Int. Cl.
| | | |
|---|---|---|
| *G16B 20/20* | (2019.01) | |
| *G16B 30/00* | (2019.01) | |
| *G16B 40/00* | (2019.01) | |
| *C12Q 1/6874* | (2018.01) | |
| *C12Q 1/6869* | (2018.01) | |

(52) U.S. Cl.
CPC ............ *G16B 20/20* (2019.02); *C12Q 1/6869* (2013.01); *C12Q 1/6874* (2013.01); *G16B 30/00* (2019.02); *G16B 40/00* (2019.02)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,210,015 A | 5/1993 | Gelfand et al. | |
| 5,399,491 A | 3/1995 | Kacian et al. | |
| 5,750,341 A | 5/1998 | Macevicz | |
| 5,854,033 A | 12/1998 | Lizardi | |
| 6,174,670 B1 | 1/2001 | Wittwer et al. | |
| 6,210,891 B1 | 4/2001 | Nyren et al. | |
| 6,258,568 B1 | 7/2001 | Nyren | |
| 6,274,320 B1 | 8/2001 | Rothberg et al. | |
| 6,404,907 B1 | 6/2002 | Gilchrist et al. | |
| 6,780,591 B2 | 8/2004 | Williams et al. | |
| 6,828,100 B1 | 12/2004 | Ronaghi | |
| 6,833,246 B2 | 12/2004 | Balasubramanian | |
| 6,911,327 B2 | 6/2005 | McMillan et al. | |
| 7,037,687 B2 | 5/2006 | Williams et al. | |
| 7,049,645 B2 | 5/2006 | Sawada et al. | |
| 7,133,782 B2 | 11/2006 | Odedra | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,323,305 B2 | 1/2008 | Leamon et al. | |
| 7,335,762 B2 | 2/2008 | Rothberg et al. | |
| 7,348,181 B2 | 3/2008 | Walt et al. | |
| 7,424,371 B2 | 9/2008 | Kamentsky | |
| 7,535,232 B2 | 5/2009 | Barbaro et al. | |
| 7,575,865 B2 | 8/2009 | Leamon et al. | |
| 7,645,596 B2 | 1/2010 | Williams et al. | |
| 7,782,237 B2 | 8/2010 | Ronaghi et al. | |
| 7,785,862 B2 | 8/2010 | Kim et al. | |
| 7,835,871 B2 | 11/2010 | Kain et al. | |
| 7,875,440 B2 | 1/2011 | Williams et al. | |
| 7,948,015 B2 | 5/2011 | Rothberg et al. | |
| 2003/0219797 A1 | 11/2003 | Zhao et al. | |

(Continued)

FOREIGN PATENT DOCUMENTS

| | | |
|---|---|---|
| GB | 2461127 | 12/2009 |
| WO | 1999/057321 | 11/1999 |

(Continued)

OTHER PUBLICATIONS

Rothberg et al. An integrated semiconductor device enabling non-optical genome sequencing Nature vol. 475 pp. 348-352 (2011).
Quail et al. A tale of three next generation sequencing platforms: comparison of Ion Torrent, Pacific Biosciences and Illumina MiSeq sequencers BMC Genomics vol. 13, article 341 (2012).
Li, H, "Mathematical Notes on SAMtools Algorithms", The Broad institute of MIT and Harvard, available at https://www.broadinstitute.org/gatk/media/docs/Samtools.pdf, dated Oct. 12, 2010, 21 pages.
Brockman et al., "Quality scores and SNP detection in sequencing-by-synthesis systems," *Genome Res.*, 18:763-770 (2008).
Chapter 2, "Machine-Learning Foundations: The Probabilistic Framework," in Baldi, P. & Brunak, S., "Bioinformatics: The Machine Learning Approach," $2^{nd}$ Ed., The MIT Press, 47-65 (2001).

(Continued)

*Primary Examiner* — John S Brusca
(74) *Attorney, Agent, or Firm* — Jones Robb, PLLC

(57) ABSTRACT

A method for evaluating variant likelihood includes: providing a plurality of template polynucleotide strands, sequencing primers, and polymerase in a plurality of defined spaces disposed on a sensor array; exposing the plurality of template polynucleotide strands, sequencing primers, and polymerase to a series of flows of nucleotide species according to a predetermined order; obtaining measured values corresponding to an ensemble of sequencing reads for at least some of the template polynucleotide strands in at least one of the defined spaces; and evaluating a likelihood that a variant sequence is present given the measured values corresponding to the ensemble of sequencing reads, the evaluating comprising: determining a measurement confidence value for each read in the ensemble of sequencing reads and modifying at least some model-predicted values using a first bias for forward strands and a second bias for reverse strands.

23 Claims, 12 Drawing Sheets
Specification includes a Sequence Listing.

(56) References Cited

U.S. PATENT DOCUMENTS

| | | |
|---|---|---|
| 2004/0018506 A1 | 1/2004 | Koehler et al. |
| 2004/0142330 A1 | 7/2004 | Nyren et al. |
| 2004/0197793 A1 | 10/2004 | Hassibi et al. |
| 2004/0197845 A1 | 10/2004 | Hassibi et al. |
| 2005/0084851 A1 | 4/2005 | Ronaghi et al. |
| 2006/0040297 A1 | 2/2006 | Leamon et al. |
| 2006/0147935 A1 | 7/2006 | Linnarsson |
| 2006/0147983 A1 | 7/2006 | O'uchi et al. |
| 2007/0059733 A1 | 3/2007 | Sundararajan et al. |
| 2007/0059741 A1 | 3/2007 | Kamahori et al. |
| 2007/0092872 A1 | 4/2007 | Rothberg et al. |
| 2007/0207471 A1 | 9/2007 | Osaka et al. |
| 2007/0219367 A1 | 9/2007 | Shchepinov et al. |
| 2007/0281300 A1 | 12/2007 | Russell et al. |
| 2008/0166727 A1 | 7/2008 | Esfandyarpour et al. |
| 2008/0182757 A1 | 7/2008 | Heiner et al. |
| 2008/0286762 A1 | 11/2008 | Miyahara et al. |
| 2008/0286767 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1 | 5/2009 | Rothberg et al. |
| 2009/0137404 A1 | 5/2009 | Drmanac et al. |
| 2009/0176200 A1 | 7/2009 | Wakita et al. |
| 2009/0312188 A1 | 12/2009 | Duer et al. |
| 2010/0035252 A1 | 2/2010 | Rothberg et al. |
| 2010/0035253 A1 | 2/2010 | Gordon et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2012/0264621 A1 | 10/2012 | Hubbell et al. |

FOREIGN PATENT DOCUMENTS

| | | |
|---|---|---|
| WO | 2001/001015 | 1/2001 |
| WO | 2002/020837 | 3/2002 |
| WO | 2003/020895 | 3/2003 |
| WO | 2005/040425 | 5/2005 |
| WO | 2007/098049 | 8/2007 |
| WO | 2008/076406 | 6/2008 |
| WO | 2008/092150 | 7/2008 |
| WO | 2008/092155 | 7/2008 |
| WO | 2009/158006 | 12/2009 |
| WO | 2010/047804 | 4/2010 |
| WO | 2010/075188 | 7/2010 |
| WO | 2010/077859 | 7/2010 |
| WO | 2010/117804 | 10/2010 |
| WO | 2010/138182 | 12/2010 |
| WO | 2011/064319 | 6/2011 |
| WO | 2011/120964 | 10/2011 |
| WO | 2011/156707 | 12/2011 |
| WO | 2012/058459 | 5/2012 |
| WO | 2012/138921 | 10/2012 |

OTHER PUBLICATIONS

Eltoukhy et al., "Modeling and Base-Calling for DNA Sequencing-By-Synthesis," *2006 IEEE International Conference on Acoustics, Speech, and Signal Processing*, II:1032-1035 (2006).

Garrison et al., "Haplotype-based variant detection from short-read sequencing," arXiv:1207.3907v2, pp. 1-9 (Jul. 20, 2012).

Ji et al., "BM-BC: A Bayesian method of base calling for Solexa sequence data," *Department pf Biostatistics, The University of Texas M. D. Andersen Cancer Center*, Houston, Texas, U.S.A. (http://odin.mdacc.tmc.edu/~ylji/BMBC/bmbc-ie2.pdf), Jan. 27, 2010.

Ledergerber et al., "Base-calling for next-generation sequencing platforms," *Briefings in Bioinformatics Advance Access*, 12(5):489-497 (Jan. 18, 2011).

Li et al., "The Sequence Alignment/Map format and SAMtools," *Bioinformatics*, 25(16):2078-2079 (2009).

Margulies et al., Supplementary Methods for the article "Genome sequencing in microfabricated high-density picolitre reactors," *Nature*, 437:376-380 (2005), pp. 1-34.

Margulies et al., "Genome sequencing in microfabricated high-density picolitre reactors," *Nature*, 437:376-380 (2005).

Massingham et al., "All Your Base: a fast and accurate probabilistic approach to base calling," *European Bioinformatics Institute, Wellcome Trust Genome Campus*, Hinxton, Cambridgeshire, UK (http://www.ebi.ac.uk/goldman-srv/AYB/references/ayb_revised.pdf), 1-26, (Oct. 26, 2011).

Meacham et al., "Identification and Correction of Systematic Error in High-Throughput Sequence Data," *BMC Bioinformatics*, 12:451, pp. 1-11 (2011).

Roche, A., "EM algorithm and variants : an informal tutorial," arXiv:1105.1476v2, pp. 1-17 (Sep. 7, 2012).

Specification & Drawings of U.S. Appl. No. 61/198,222, filed Nov. 4, 2008.

Appendix to the Specification of U.S. Appl. No. 61/198,222, filed Nov. 4, 2008.

METHODS, SYSTEMS, AND COMPUTER READABLE MEDIA FOR EVALUATING VARIANT LIKELIHOOD

CROSS-REFERENCE TO RELATED APPLICATIONS

This application is a continuation application of U.S. application Ser. No. 14/200,942, filed Mar. 7, 2014 (now abandoned), which claims the benefit of U.S. Prov. Pat. Appl. No. 61/782,240, filed Mar. 14, 2013, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Aug. 25, 2022, is named TP103013USCON1_SL.txt and is 838 bytes in size.

FIELD

This application generally relates to methods, systems, and computer readable media for nucleic acid sequencing, and, more specifically, to methods, systems, and computer readable media for evaluating variant likelihood in nucleic acid sequencing.

BACKGROUND

Nucleic acid sequencing data may be obtained in various ways, including using next-generation sequencing systems such as, for example, the Ion PGM™ and Ion Proton™ systems implementing Ion Torrent™ sequencing technology; see, e.g., U.S. Pat. No. 7,948,015 and U.S. Pat. Appl. Publ. Nos. 2010/0137143, 2009/0026082, and 2010/0282617, which are all incorporated by reference herein in their entirety. There is a need for new methods, systems, and computer readable media that can better evaluate variant likelihood and reduce sequencing errors when analyzing data obtained using these or other sequencing systems/platforms.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

SUMMARY

Figure 1:
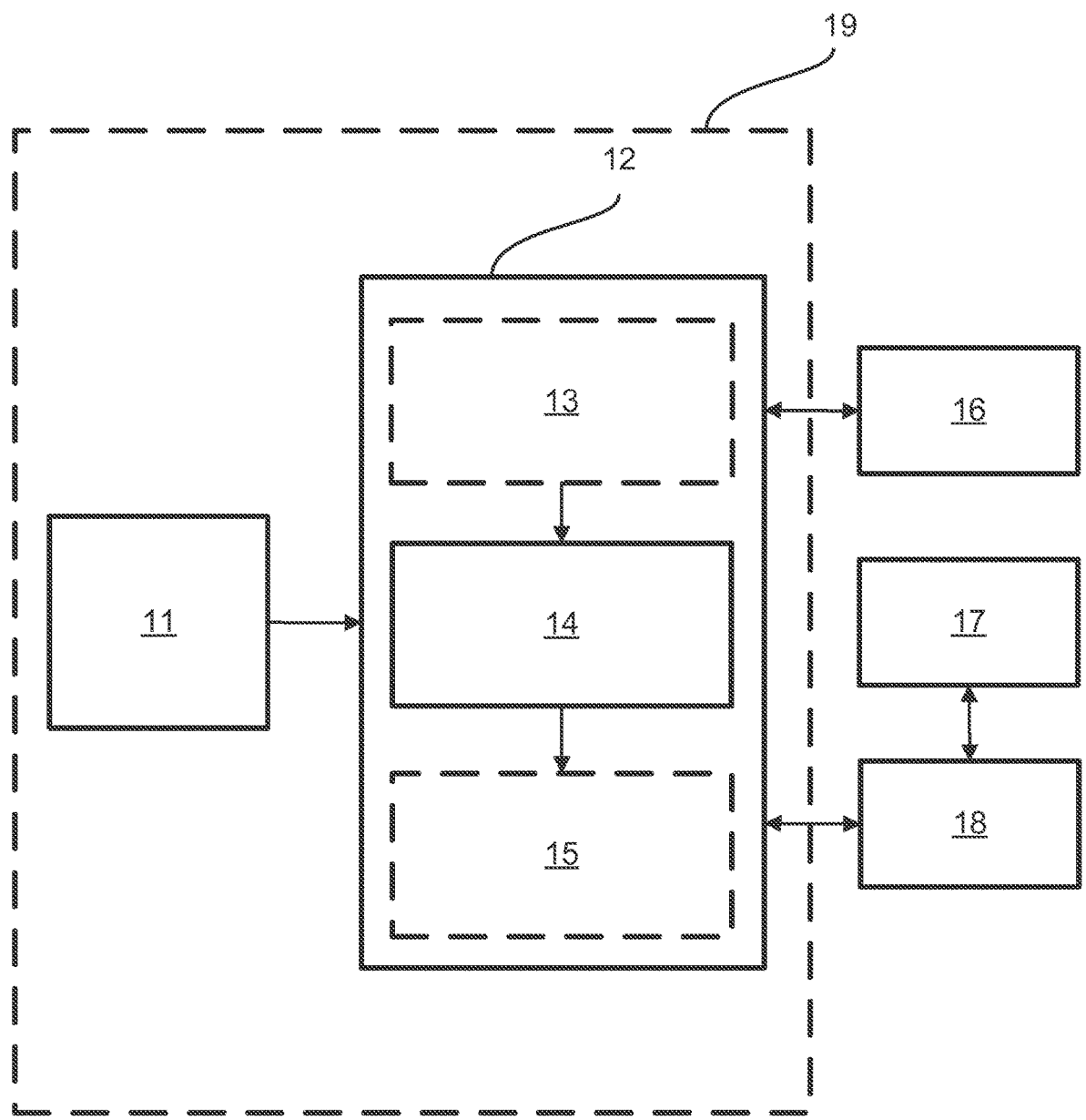
FIG. 1 illustrates an exemplary system for evaluating variant likelihood.

According to an exemplary embodiment, there is provided a method for evaluating variant likelihood in nucleic acid sequencing, comprising: (a) providing a plurality of template polynucleotide strands, sequencing primers, and polymerase in a plurality of defined spaces disposed on a sensor array; (b) exposing the plurality of template polynucleotide strands, sequencing primers, and polymerase to a series of flows of nucleotide species according to a predetermined order; (c) obtaining measured values corresponding to an ensemble of sequencing reads for at least some of the template polynucleotide strands in at least one of the defined spaces; and (d) evaluating a likelihood that a variant sequence is present given the measured values corresponding to the ensemble of sequencing reads, the evaluating comprising: (i) determining a measurement confidence value for each read in the ensemble of sequencing reads, wherein the determining is based on variations between the measured values and model-predicted values for hypothesized sequences obtained using a predictive model of nucleotide incorporations responsive to flows of nucleotide species; and (ii) modifying at least some model-predicted values using a first bias for forward strands and a second bias for reverse strands, wherein the modifying is based on variations between model-predicted values for different hypothesized sequences obtained using the predictive model of nucleotide incorporations responsive to flows of nucleotide species.

According to an exemplary embodiment, there is provided a non-transitory machine-readable storage medium comprising instructions which, when executed by a processor, cause the processor to perform a method for evaluating variant likelihood in nucleic acid sequencing comprising: (a) obtaining measured values corresponding to an ensemble of sequencing reads for at least some template polynucleotide strands in at least one defined space, wherein a plurality of template polynucleotide strands, sequencing primers, and polymerase have been provided in a plurality of defined spaces disposed on a sensor array, and wherein the plurality of template polynucleotide strands, sequencing primers, and polymerase have been exposed to a series of flows of nucleotide species according to a predetermined order; and (b) evaluating a likelihood that a variant sequence is present given the measured values corresponding to the ensemble of sequencing reads, the evaluating comprising: (i) determining a measurement confidence value for each read in the ensemble of sequencing reads, wherein the determining is based on variations between the measured values and model-predicted values for hypothesized sequences obtained using a predictive model of nucleotide incorporations responsive to flows of nucleotide species; and (ii)

modifying at least some model-predicted values using a first bias for forward strands and a second bias for reverse strands, wherein the modifying is based on variations between model-predicted values for different hypothesized sequences obtained using the predictive model of nucleotide incorporations responsive to flows of nucleotide species.

According to an exemplary embodiment, there is provided a system for evaluating variant likelihood in nucleic acid sequencing, including: a plurality of template polynucleotide strands, sequencing primers, and polymerase provided in a plurality of defined spaces disposed on a sensor array; an apparatus configured to expose the plurality of template polynucleotide strands, sequencing primers, and polymerase to a series of flows of nucleotide species according to a predetermined order; a machine-readable memory; and a processor configured to execute machine-readable instructions, which, when executed by the processor, cause the system to perform a method for evaluating variant likelihood, comprising: (a) obtaining measured values corresponding to an ensemble of sequencing reads for at least some of the template polynucleotide strands in at least one of the defined spaces; and (b) evaluating a likelihood that a variant sequence is present given the measured values corresponding to the ensemble of sequencing reads, the evaluating comprising: (i) determining a measurement confidence value for each read in the ensemble of sequencing reads, wherein the determining is based on variations between the measured values and model-predicted values for hypothesized sequences obtained using a predictive model of nucleotide incorporations responsive to flows of nucleotide species; and (ii) modifying at least some model-predicted values using a first bias for forward strands and a second bias for reverse strands, wherein the modifying is based on variations between model-predicted values for different hypothesized sequences obtained using the predictive model of nucleotide incorporations responsive to flows of nucleotide species.

EXEMPLARY EMBODIMENTS

The following description and the various embodiments described herein are exemplary and explanatory only and are not to be construed as limiting or restrictive in any way. Other embodiments, features, objects, and advantages of the present teachings will be apparent from the description and accompanying drawings, and from the claims.

The identification of sequence variants, including single nucleotide polymorphism (SNPs), insertions, and/or deletions, is an important application of next-generation sequencing technologies. The particular approach/technology used to obtain sequencing data and the particular data analysis approach/methods used to analyze the sequencing data can both affect the accuracy of sequence variant identification. For example, the use of alignment methodologies developed and operating in base space can sometimes lead to insertions or deletions in the alignment of reads obtained using sequencing-by-synthesis technologies that operate at least to some extent in flow space.

According to various exemplary embodiments, methods, systems, and computer readable media for evaluating variant likelihood in nucleic acid sequencing are disclosed herein. The various embodiments provide a more generalized method for inferring variant likelihood by considering properties of ensemble of reads. In some cases, such as a SNP or simple indel affecting one or two flows, the ability to infer the confidence of a read without referring to the ensemble is high because bias is expected to be low and variation should be well-estimated. However, in other cases, such as some multi-nucleotide repeats or short indels in long homopolymer stretches, estimating bias and variance is critical to avoid false positives, and it may then be beneficial to consider the ensemble in addition to each read to evaluate confidence.

Variant Frequency Framework

A fundamental problem in variant calling is to assign a posterior distribution to a variant frequency given an observed ensemble of reads. The reads that strongly support a sequence provide information about the frequency of that sequence while those that weakly support the sequence provide little information. However, under reasonable assumptions about systematic error, the strength of support for a sequence is itself conditional on the ensemble of reads observed. In various embodiments, one may estimate both the error structure for a particular ensemble of reads and the plausible distribution of variants.

In an example, let $V_1$ and $V_2$ represent two possible sequences, and let $\pi$ represent the frequency of $V_1$ and $(1-\pi)$ represent the frequency of $V_2$. Further, let $R_1, R_2, \ldots, R_N$ represent N measured reads, and let each read have a measurement confidence value of being $V_1$ of $\epsilon_i$. The likelihood of observing the N reads conditional on a given frequency, $L(R_1, R_2, \ldots, R_N|\pi)$, which is a function of a product between the prior and the likelihood of each measured read under a given value of $\pi$, may be expressed as follows:

$$L(R_1, R_2, \ldots, R_N \mid \pi) = c * P(\pi) * \prod_{i=1}^{N} (\pi * \epsilon_i + (1 - \pi) * (1 - \epsilon_i))$$

where: c is a normalization constant; $P(\pi)$ represents a prior probability of $\pi$; i is an integer between 1 and N identifying a sequencing read; and N is an integer specifying a number of sequencing reads in the ensemble. In various embodiments, the distribution of the frequency $\pi$ and the confidence values $\epsilon_i$, which are unknown, may be inferred based on the data for downstream hypothesis evaluation.

In another example, let $V_1$ and $V_2$ represent two possible sequences, let $\pi$ represent the frequency of $V_1$ and $(1-\pi)$ represent the frequency of $V_2$, and let $(1-\tau)$ represent a frequency of an outlier event. (Because of the strong likelihood that there are outlier measurements in any collection of reads (e.g., due to misalignment), it can be useful to postulate a third possibility covering such outlier events.) Further, let $R_1, R_2, \ldots, R_N$ represent N measured reads, and let each read have a measurement confidence value of being $V_1$ of $\epsilon_i$. The likelihood of observing the N reads conditional on given frequencies $\pi$ and $\tau$, $L(R_1, R_2, \ldots, R_N|\tau)$, which is a function of a product between the prior and the likelihood of each measured read under given values of $\pi$ and $\tau$, may be expressed as follows:

$$L(R_1, R_2, \ldots, R_N \mid \pi, \tau) =$$
$$c * P(\pi) * \prod_{i=1}^{N} (\tau * (\pi * \epsilon_i + (1 - \pi) * (1 - \epsilon_i)) + (1 - \tau) * T)$$

where: c is a normalization constant; T represents a density of the outlier event; $P(\pi)$ represents a prior probability of $\pi$; i is an integer between 1 and N identifying a sequencing read; and N is an integer specifying a number of sequencing reads in the ensemble. In various embodiments, the distribution of the frequencies π and (1−τ) and the confidence values $\epsilon_i$, which are unknown, may be inferred based on the data for downstream hypothesis evaluation. In some embodiments, the frequency (1−τ) may be assumed to have an (improper) flat density across all reads.

Confidence Values

In the above framework, the likelihood of observing the N reads depends on the measurement confidence values $\epsilon_i$ in addition to the frequency π (and outlier frequency τ if included). The measurement confidence values $\epsilon_i$ could be estimated using methods known in the art for evaluating confidence values, which typically would be read-specific and not specifically adapted to a particular underlying sequencing technology. Preferably, however, in an embodiment the confidence values $\epsilon_i$ may be derived or estimated using ensembles of reads along with predictive models related to the underlying sequencing technology.

In an example, let $m_{i1}, m_{i2}, \ldots, m_{ij}, \ldots, m_{iM}$ represent a vector of measured values for M nucleotide flows associated with an i-th read (e.g., a set of normalized, calibrated values observed for the i-th read over the M flows), and let $p_{i1}, p_{i2}, \ldots, p_{ij}, \ldots, p_{iM}$ represent a vector of predicted values for the i-th read over the M flows under a predictive model. Any suitable predictive model may be used, recognizing of course that more accurate models are likely to yield better results. The model may be selected depending on the underlying sequencing technology and may, for example, be a model as described in Davey et al., U.S. Pat. Appl. Publ. No. 2012/0109598, published on May 3, 2012, and/or Sikora et al., U.S. Pat. Appl. Publ. No. 2013/0060482, published on Mar. 7, 2012, which are all incorporated by reference herein in their entirety.

Regardless of what predictive model is being used, there will be some variation between measured and predicted values. In some cases, it may be useful to make certain approximations characterizing the variation. In an example, one may make the approximation that the difference between the measured and predicted values are normally and independently distributed in each flow with a mean of zero and a variance given by $\sigma_{ij}^2$ so that $\delta_{ij}^x = m_{ij}^x - p_{ij}^x \sim N(0, \sigma_{ij}^2)$ for the i-th read and the j-th flow (where the x superscript denotes an index of some hypothesized sequence $V_x$). In another example, which may be of particular use in cases including outliers that may result in heavy-tailed phenomena, the normal/gaussian likelihood model may be too light-tailed and a t-distribution may better reflect the heavy-tailed phenomena.

In various embodiments, given measured sequencing data, a suitable predictive model, and some approximation characterizing the distribution of differences between measured and predicted values, $\delta_{ij}^x$ may be calculated and $\sigma_{ij}^2$ may be estimated using any suitable method for fitting data to a distribution (or preferably as further discussed in this and/or the next sections). In turn, $\delta_{ij}^2$ and $\sigma_{ij}^2$ may be used to calculate various statistical measures that may be used to obtain estimates of the measurement confidence values $\epsilon_i$.

In various embodiments, the statistical measures may be log-likelihood contributions. For example, the log-likelihood contribution for the j-th flow conditional on $V_x$ (neglecting constants), $LL_{xj}$, may be expressed as $LL_{xj} = -\ln(\sigma_{ij}) + (\delta_{ij}^2/(2*\sigma_{ij}^2))$. The log-likelihood of the measured values under hypothesis x may then be expressed as $LL_x = \Sigma_j LL_{xj}$, the sum of the contributions of all flows for the particular read. Finally, the log-likelihood contributions under two sequence hypotheses may be used to estimate $\epsilon_1$ using the following expression:

$$\epsilon_i = \frac{\exp(LL_{xi})}{\exp(LL_{xi}) + \exp(LL_{yi})} = \frac{1}{1 + \exp(LL_{yi} - LL_{xi})}.$$

It should be noted that the above embodiments provide an underspecified parameter set as the variances within the observed reads are unknown. One could estimate the variances (e.g., using flows at which the predictions do not differ), which would effectively amount to treating each read independently. However, while this might be computationally convenient, such a simplification does not fit the data, which suggest for example that variances for flows with large measured values are larger than variances for flows with small measured values.

In various embodiments, the variation in measurements may be estimated by exploiting the information across the ensemble of reads to better estimate the confidence within each read. In an example, each read may be assigned a division of responsibility $\rho_i$ for each sequence based on both the likelihood and the base rate to obtain an estimate of variation for a given division of responsibility. In an embodiment, the measurement confidence values $\epsilon_1$ in the likelihood of observing the N reads conditional on a given frequency may be measures of responsibilities $\rho_i$.

In various embodiments, given measured sequencing data, one may estimate π using any suitable estimation method, and, given a suitable predictive model and some approximation characterizing the distribution of differences between measured and predicted values, $\delta_{ij}^x$ may be calculated and $\sigma_{ij}^2$ may be estimated using any suitable method for fitting data to a distribution (or preferably as further discussed in this and/or the next section). In turn, π, $\delta_{ij}^x$ and $\sigma_{ij}^2$ may be used to calculate various statistical measures that may be used to obtain estimates of the measures of responsibility $\rho_i$.

In various embodiments, the statistical measures may be log-likelihood contributions. For example, the log-likelihood contribution for the j-th flow conditional on $V_x$ (neglecting constants), $LL_{xj}$, may be expressed as $LL_{xj} = -\ln(\sigma_{ij}) + (\delta_{ij}^2/(2*\sigma_{ij}^2))$. The log-likelihood of the measured values under hypothesis x may then be expressed as $LL_x = \Sigma_j LL_{xj}$, the sum of the contributions of all flows for the particular read. Finally, the log-likelihood contributions under two sequence hypotheses may be used to estimate $\rho_i$ using the following expression:

$$\rho_i = \frac{\pi}{\pi + (1 - \pi) * \exp(LL_{yi} - LL_{xi})}.$$

Under the division of responsibility framework, the quantity determining the variance relevant to the sequence change of interest is then the expected value of the squared deviation across reads. In various embodiments, the variance $\hat{\sigma}^2$ may be estimated using the evaluated $\delta_{ij}^x$ and estimated $\rho_i$, using the following expression:

$$\hat{\sigma}^2 = \frac{\sum_{i=1}^{N} \left( \rho_i \sum_{j=1}^{M} (\delta_{ij}^x)^2 + (1 - \rho_i) \sum_{j=1}^{M} (\delta_{ij}^y)^2 \right)}{N}.$$

Estimation of Variance

Because the variance around predictions can vary significantly across different reads and flows, it is preferable to estimate $\sigma_{ij}^2$, the variance for the j-th flow in the i-th read. In an embodiment, this may be achieved by decomposing the variance in any flow and read in terms of some underlying latent components: $\sigma_{ij}^2 = \Sigma_{m=1}^K (\varphi_{oijm} * \sigma_m^2)$, where $\varphi_{ijm}$ is a proportionality constant determining the amount of variation contributed by the m-th latent component.

The components may be defined in various ways. For example, the components $\sigma_m^2$ may consist of $\sigma_\varphi^2$ (the variance contributed to a flow by simply existing without any reference to incorporation), $\sigma_x^2$ (a term for incorporation components not explicitly modeled), and then all the other components. Alternatively, the components $\sigma_m^2$ may correspond to each integer homopolymer length. Alternatively, the components $\sigma_m^2$ may be defined according to the polymerase state variables (e.g., 10% of the variance is provided by a given base or homopolymer run in the hypothesis in a given flow) and fitted according to variation contributed by a genomic location.

The components may be approximated in various ways. For example, initial estimates for the latent variables may be updated using an expectation-maximization (EM) methodology and a method-of-moments approximation. Under the decomposition above, estimates $\sigma_{kn}^2 = (\Sigma(\omega_i * r_{ij}^2))/(\Sigma(\varphi_{ijm}))$, where $\omega_{ij} = ((\varphi_{ijm} * \sigma_{k,n-1}^2)/(\Sigma(\varphi_{ijm} * \sigma_{m,n-1}^2))$, for the k-th component may be updated using the proportion of variance attributed to each read and flow. This can be done relatively quickly by iterating only over relevant flows for each component. Here, the use of a multiplicative proportion of each squared residual to estimate the contribution towards the component ensures that estimates are always positive for variances.

Overall Likelihood

In various embodiments, putting all the above together, the likelihood $L(R_1, R_2, \ldots, R_N | \pi)$ of observing the N reads may be maximized, repeatedly, by estimating (i) the frequency $\pi$ (and outlier frequency $\tau$ if included), (ii) either the measurement confidence values $\epsilon_i$ (which may be functions of $\delta_{ij}^2$ and $\sigma_{ij}^2$ as described above) or the measures of responsibility $\rho_i$ (which may be functions of $\pi$, $\delta_{ij}^2$, and $\sigma_{ij}^2$ as described above), and (iii) the variances $\sigma_{ij}^2$ (which may be expressed various ways in terms of latent components as described above) individually conditional on the values of the others and the observed data. This may be done using any suitable statistical method for obtaining maximum likelihood and/or maximum a posteriori estimates of some or all of these parameters given the observed data and any underlying assumptions, including for example estimating the variance iteratively using an expectation-maximization algorithm and a method-of-moments approximation. In an embodiment, after starting with initial estimates, the likelihood may be first maximized based on $\pi$ while holding $\epsilon_i$ (or $\rho_i$) and $\sigma_{ij}^2$ fixed, then based on $\epsilon_i$ (or $\rho_i$) while holding $\pi$ and $\sigma_{ij}^2$ fixed, then based on $\sigma_{ij}^2$ while holding $\pi$ and $\epsilon_i$ (or $\rho_i$) fixed, and then iterating as needed. Assuming reasonable stability of estimating the variance, the posterior distribution for the variant frequency conditional on the maximum a posteriori value of the variance may then be obtained. Descriptions of methods for finding maximum likelihood or maximum a posteriori estimates of a plurality of parameters in a statistical model, including the expectation-maximization algorithm and other algorithms, may be found in various statistical papers, such as Dempster et al., "Maximum Likelihood from Incomplete Data via the EM Algorithm," Journal of the Royal Statistical Society Series B, 39(1):1-38 (1977); and Roche, "EM algorithm and variants: an informal tutorial," arXiv:1105.1476v2 [stat.CO] (2012) (available at http://arxiv.org/abs/1105.1476v2).

Systematic Biases

In various embodiments, variant calling may be further improved by capturing systematic bias between the measurements and predicted values (e.g., systematic underestimating of predicted values that may lead to systematic undercalls) that may affect the ability to distinguish between sequence hypotheses. In the present context, the relevant bias in measurements for purposes of assigning responsibility is a component lying along the discriminant vector d of length M for a given read $R_i$ having components $d_j = p_j^x - p_j^y$, which are the differences in measurements predicted under the two hypothesized sequences x and y.

In an example, a predicted value for each read may be modified by applying a transformation $q_j^x = p_j^x + \beta_f * d_j$ for forward strands and a transformation $q_j^x = p_j^x + \beta_r * d_j$ for reverse strands, where: $q_j^x$ represents modified predicted values for a given sequencing read at flow j under hypothesized sequence x; $\beta_f$ denotes the first bias for forward strands; $\beta_r$ denotes the second bias for reverse strands; $p_j^x$ and $p_j^y$ represent predicted values for the given sequencing read at flow j under hypothesized sequences x and y, respectively; j is an integer between 1 and M; and M represents a number of flows.

The biases may be estimated in various ways. In an embodiment, the two biases may be inferred from the data together with (i) the frequency $\pi$ (and outlier frequency $\tau$ if included), (ii) either the measurement confidence values $\epsilon_i$ (which may be functions of $\delta_{ij}^2$ and $\sigma_{ij}^2$ as described above) or the measures of responsibility $\rho_i$ (which may be functions of $\pi$, $\delta_{ij}^2$, and $\sigma_{ij}^2$ as described above), and (iii) the variances $\sigma_{ij}^2$ (which may be expressed various ways in terms of latent components as described above) individually conditional on the values of the others and the observed data. As above, this may be done using any suitable statistical method for obtaining maximum likelihood and/or maximum a posteriori estimates of some or all of these parameters given the observed data and any underlying assumptions, including by iteratively maximizing over one variable while holding the others fixed. In addition, one may assign a prior to the bias, which may be a normal distribution with mean zero and variance $1/t^2$ (that is, $N(0, 1/t^2)$), where t is the approximate precision of the bias term, which may be learned within an experiment by exploiting the fact that most positions are reference. The bias maximizing the likelihood conditional on the other latent variables may be determined using the following expression:

$$\beta_f = \left( \sum \frac{d_{ij}^2}{\sigma_{ij}^2} \right)^{-1} * \left( \sum \frac{d_{ij}^2 * (\rho_i * (m_{ij} - p_{ij}^x) + (1 - \rho_i) * (m_{ij} - p_{ij}^y))}{\sigma_{ij}^2} \right),$$

where the sum is taken over all reads on the forward strand and all relevant flows. (This is the projection of the residuals onto the discriminant vector d, weighted by the responsibility $\rho_i$ of each read for each sequence.) The bias on the reads mapping to the reverse strand may be estimated similarly, except that the sum is then taken over all reads on the reverse strand and all relevant flows. A shrinkage term $1/t^2$ may be added to the denominator to shrink the bias estimate towards zero, thus incorporating the prior. The shrinkage term essentially acts as a tuning parameter for the precision of the bias prior. If set high, the approach reduces to the case without bias being postulated, as the bias becomes zero, as in the case of independent reads.

FIG. 1 illustrates an exemplary system for evaluating variant likelihood. The exemplary system includes an apparatus or sub-system for nucleic acid sequencing and/or analysis 11, a computing server/node/device 12 including a variant calling engine 14, and a display 16, which may be internal and/or external. The apparatus or sub-system for nucleic acid sequencing and/or analysis 11 may be any type of instrument that can generate nucleic acid sequence data from nucleic acid samples, which may include a nucleic acid sequencing instrument, a real-time/digital/quantitative PCR instrument, a microarray scanner, etc. The computing server/node/device 12 may be a workstation, mainframe computer, distributed computing node (part of a "cloud computing" or distributed networking system), personal computer, mobile device, etc. The computing server/node/device 12 may be configured to host a pre-variant calling processing engine 13, which may be configured to include various signal/data processing modules that may be configured to receive signal/data from the apparatus or sub-system for nucleic acid sequencing and/or analysis 11 and perform various processing steps, such as conversion from flow space to base space, determination of base calls, determination of base call quality values, preparation of read data for use by a mapping module, and/or alignment and/or mapping of reads to a reference sequence or genome, which may be a whole/partial genome, whole/partial exome, etc. The exemplary system may also include a client device terminal 17, which may include a data analysis API and may be communicatively connected to the computing server/node/device 12 via a network connection 18 that may be a "hardwired" physical network connection (e.g., Internet, LAN, WAN, VPN, etc.) or a wireless network connection (e.g., Wi-Fi, WLAN, etc.). The exemplary system may also include a post-variant calling processing engine 15, which may be configured to include various signal/data processing modules that may be configured to apply post-processing to variant calls, which may include annotating various variant calls and/or features, converting data from flow space to base space, filtering of variants (e.g., based on a minimum score threshold, a minimum number of reads including the variant, a minimum frequency of reads including the variant, a minimum mapping quality, a strand probability, and region filtering, for example), and formatting the variant data for display or use by client device terminal 17. In an embodiment, the apparatus or sub-system for nucleic acid sequencing and/or analysis 11 and the computing server/node/device 12 may be integrated into a single instrument or system comprising components present in a single enclosure 19. The client device terminal 17 may be configured to communicate information to and/or control the operation of the computing server/node/device 12 and its modules and/or operating parameters.

Sequencing Instrumentation

Figure 2:
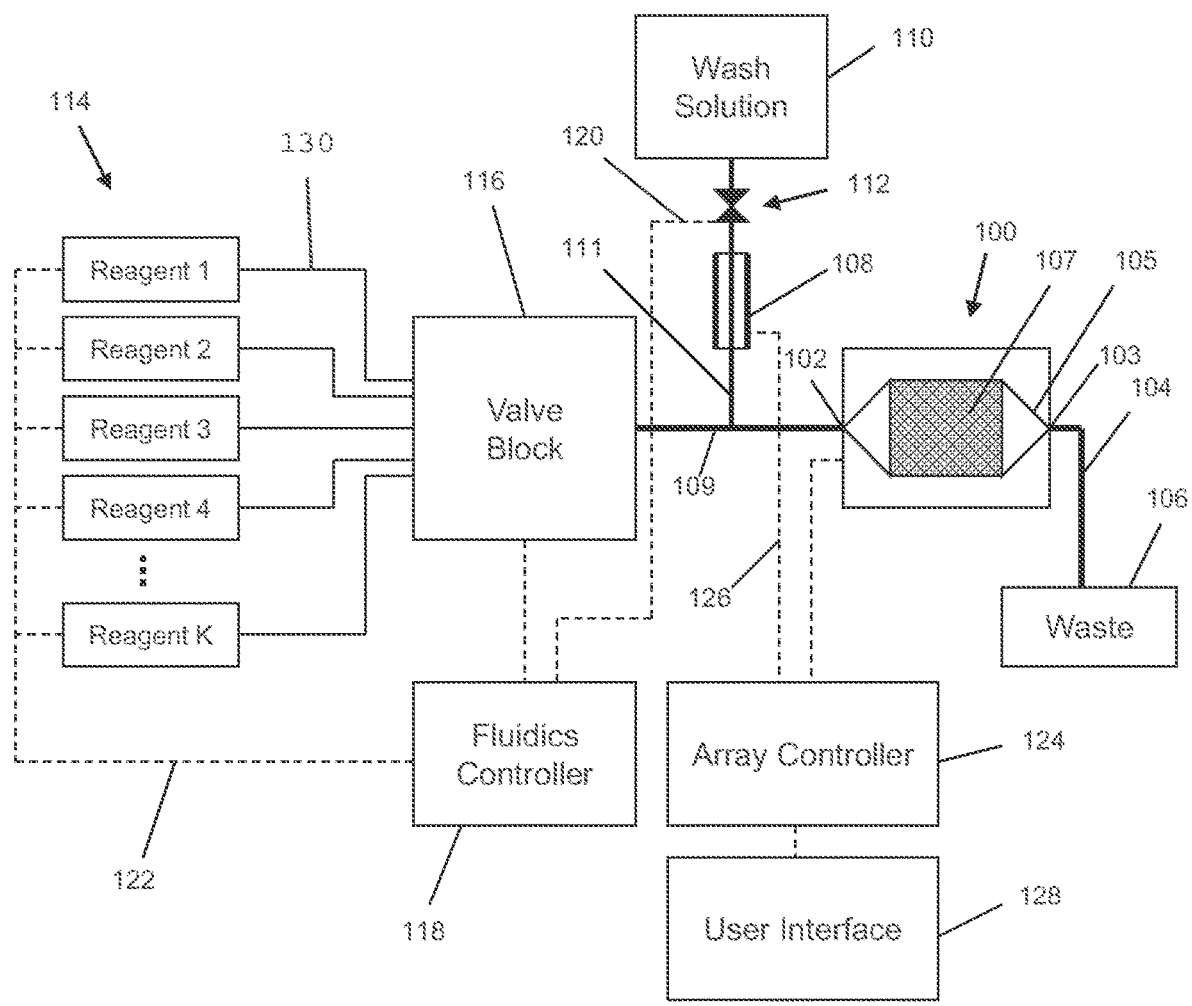
FIG. 2 illustrates components of an exemplary apparatus for nucleic acid sequencing.

FIG. 2 illustrates components of an exemplary apparatus for nucleic acid sequencing. The components include a flow cell and sensor array 100, a reference electrode 108, a plurality of reagents 114, a valve block 116, a wash solution 110, a valve 112, a fluidics controller 118, lines 120/122/126, passages 104/109/111, a waste container 106, an array controller 124, and a user interface 128. The flow cell and sensor array 100 includes an inlet 102, an outlet 103, a microwell array 107, and a flow chamber 105 defining a flow path of reagents over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100. The reagents 114 may, for example, contain dNTPs to be flowed through passages 130 and through the valve block 116, which may control the flow of the reagents 114 to flow chamber 105 (also referred to herein as a reaction chamber) via passage 109. The system may include a reservoir 110 for containing a wash solution that may be used to wash away dNTPs, for example, that may have previously been flowed. The microwell array 107 may include an array of defined spaces, such as microwells, for example, that is operationally associated with a sensor array so that, for example, each microwell has a sensor suitable for detecting an analyte or reaction property of interest. The microwell array 107 may preferably be integrated with the sensor array as a single device or chip. The array controller 124 may provide bias voltages and timing and control signals to the sensor, and collect and/or process output signals. The user interface 128 may display information from the flow cell and sensor array 100 as well as instrument settings and controls, and allow a user to enter or set instrument settings and controls. The valve 112 may be shut to prevent any wash solution 110 from flowing into passage 109 as the reagents are flowing. Although the flow of wash solution may be stopped, there may still be uninterrupted fluid and electrical communication between the reference electrode 108, passage 109, and the sensor array 107. The distance between the reference electrode 108 and the junction between passages 109 and 111 may be selected so that little or no amount of the reagents flowing in passage 109 and possibly diffusing into passage 111 reach the reference electrode 108. In various embodiments, the fluidics controller 118 may be programmed to control driving forces for flowing reagents 114 and the operation of valve 112 and valve block 116 to deliver reagents to the flow cell and sensor array 100 according to a predetermined reagent flow ordering.

In this application, "defined space" generally refers to any space (which may be in one, two, or three dimensions) in which at least some of a molecule, fluid, and/or solid can be confined, retained and/or localized. The space may be a predetermined area (which may be a flat area) or volume, and may be defined, for example, by a depression or a micro-machined well in or associated with a microwell plate, microtiter plate, microplate, or a chip, or by isolated hydrophobic areas on a generally hydrophobic surface. Defined spaces may be arranged as an array, which may be a substantially planar one-dimensional or two-dimensional arrangement of elements such as sensors or wells. Defined spaces, whether arranged as an array or in some other configuration, may be in electrical communication with at least one sensor to allow detection or measurement of one or more detectable or measurable parameter or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information or signal about a chemical reaction or desired association event, for example, a nucleotide incorporation event and/or a related ion concentration (e.g., a pH measurement). The sensors may include at least one ion sensitive field effect transistor ("ISFET") or chemically sensitive field effect transistor ("chemFET").

Figure 3:
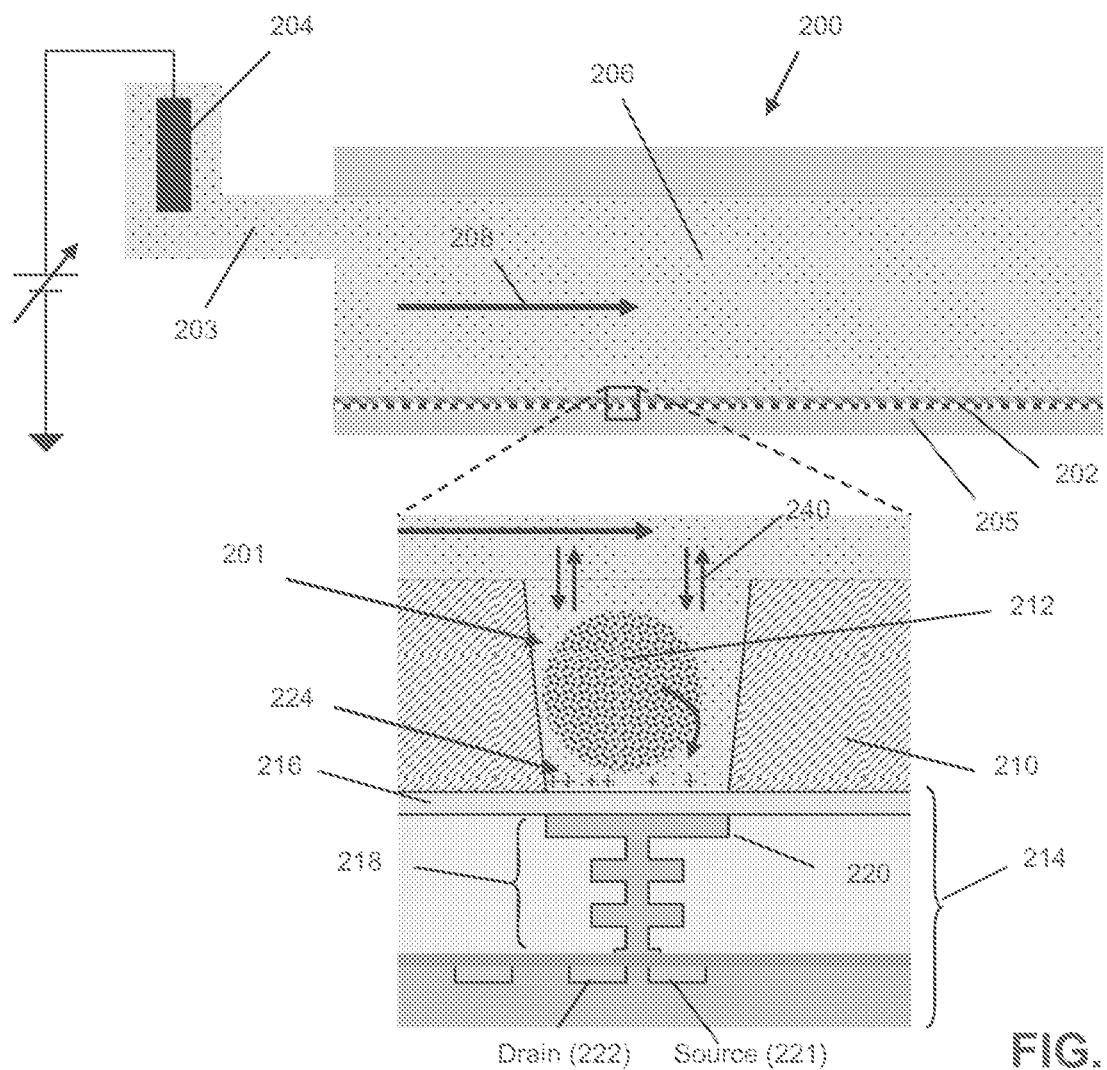
FIG. 3 illustrates an exemplary flow cell for nucleic acid sequencing.

FIG. 3 illustrates an exemplary flow cell for nucleic acid sequencing. The flow cell 200 includes a microwell array 202, a sensor array 205, and a flow chamber 206 in which a reagent flow 208 may move across a surface of the microwell array 202, over open ends of microwells in the microwell array 202. The flow of reagents (e.g., nucleotide species) can be provided in any suitable manner, including delivery by pipettes, or through tubes or passages connected to a flow chamber. A microwell 201 in the microwell array 202 may have any suitable volume, shape, and aspect ratio. A sensor 214 in the sensor array 205 may be an ISFET or a chemFET sensor with a floating gate 218 having a sensor plate 220 separated from the microwell interior by a passivation layer 216, and may be predominantly responsive to (and generate an output signal related to) an amount of charge 224 present on the passivation layer 216 opposite of the sensor plate 220. Changes in the amount of charge 224 cause changes in the current between a source 221 and a drain 222 of the sensor 214, which may be used directly to provide a current-based output signal or indirectly with additional circuitry to provide a voltage output signal. Reactants, wash solutions, and other reagents may move into microwells primarily by diffusion 240. One or more analytical reactions to identify or determine characteristics or properties of an analyte of interest may be carried out in one or more microwells of the microwell array 202. Such reactions may generate directly or indirectly by-products that affect the amount of charge 224 adjacent to the sensor plate 220. In an embodiment, a reference electrode 204 may be fluidly connected to the flow chamber 206 via a flow passage 203. In an embodiment, the microwell array 202 and the sensor array 205 may together form an integrated unit forming a bottom wall or floor of the flow cell 200. In an embodiment, one or more copies of an analyte may be attached to a solid phase support 212, which may include microparticles, nanoparticles, beads, gels, and may be solid and porous, for example. The analyte may include one or more copies of a nucleic acid analyte obtained using any suitable technique.

Figure 4:
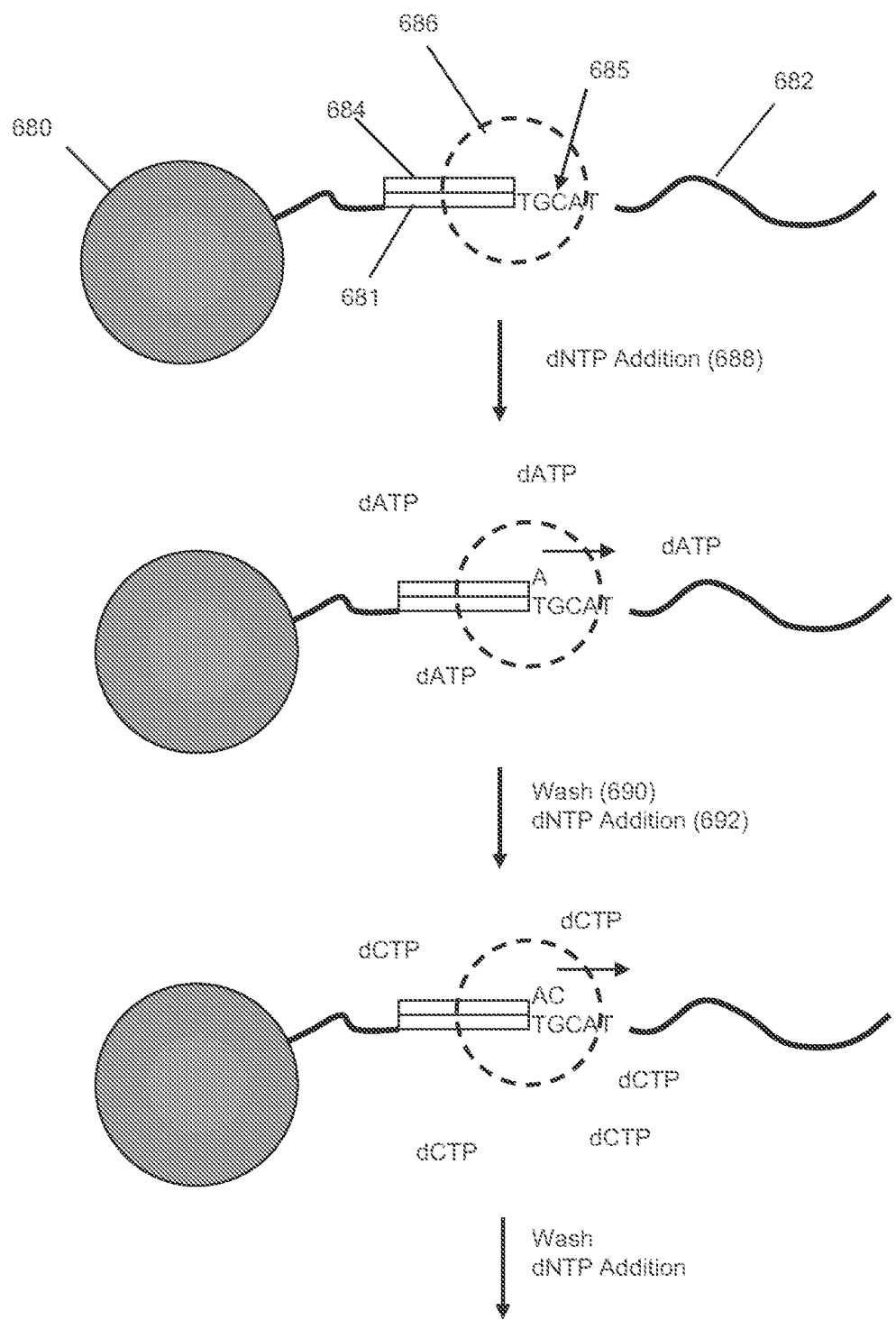
FIG. 4 illustrates an exemplary process for label-free, pH-based sequencing.

FIG. 4 illustrates an exemplary process for label-free, pH-based sequencing. A template 682 with sequence 685 and a primer binding site 681 are attached to a solid phase support 680. The template 682 may be attached as a clonal population to a solid support, such as a microparticle or bead, for example, and may be prepared as disclosed in Leamon et al., U.S. Pat. No. 7,323,305. In an embodiment, the template may be associated with a substrate surface or present in a liquid phase with or without being coupled to a support. A primer 684 and DNA polymerase 686 are annealed to the template 682 so that the primer's 3' end may be extended by a polymerase and that a polymerase is bound to such primer-template duplex (or in close proximity thereof) so that binding and/or extension may take place when dNTPs are added. In step 688, dNTP (shown as dATP) is added, and the DNA polymerase 686 incorporates a nucleotide "A" (since "T" is the next nucleotide in the template 682 and is complementary to the flowed dATP nucleotide). In step 690, a wash is performed. In step 692, the next dNTP (shown as dCTP) is added, and the DNA polymerase 686 incorporates a nucleotide "C" (since "G" is the next nucleotide in the template 682). More details about pH-based nucleic acid sequencing may be found in U.S. Pat. No. 7,948,015 and U.S. Pat. Appl. Publ. Nos. 2010/0137143, 2009/0026082, and 2010/0282617.

In an embodiment, the primer-template-polymerase complex may be subjected to a series of exposures of different nucleotides in a pre-determined sequence or ordering. If one or more nucleotides are incorporated, then the signal resulting from the incorporation reaction may be detected, and after repeated cycles of nucleotide addition, primer extension, and signal acquisition, the nucleotide sequence of the template strand may be determined. The output signals measured throughout this process depend on the number of nucleotide incorporations. Specifically, in each addition step, the polymerase extends the primer by incorporating added dNTP only if the next base in the template is complementary to the added dNTP. With each incorporation, an hydrogen ion is released, and collectively a population released hydrogen ions change the local pH of the reaction chamber. The production of hydrogen ions may be monotonically related to the number of contiguous complementary bases (e.g., homopolymers) in the template. Deliveries of nucleotides to a reaction vessel or chamber may be referred to as "flows" of nucleotide triphosphates (or dNTPs). For convenience, a flow of dATP will sometimes be referred to as "a flow of A" or "an A flow," and a sequence of flows may be represented as a sequence of letters, such as "ATGT" indicating "a flow of dATP, followed by a flow of dTTP, followed by a flow of dGTP, followed by a flow of dTTP." The predetermined ordering may be based on a cyclical, repeating pattern consisting of consecutive repeats of a short pre-determined reagent flow ordering (e.g., consecutive repeats of pre-determined sequence of four nucleotide reagents such as, for example, "ACTG ACTG . . . "), may be based in whole or in part on some other pattern of reagent flows (such as, e.g., any of the various reagent flow orderings discussed herein and/or in Hubbell et al., U.S. Pat. Appl. Publ. No. 2012/0264621, published Oct. 18, 2012, which is incorporated by reference herein in its entirety), and may also be based on some combination thereof.

In various embodiments, output signals due to nucleotide incorporation may be processed, given knowledge of what nucleotide species were flowed and in what order to obtain such signals, to make base calls for the flows and compile consecutive base calls associated with a sample nucleic acid template into a read. A base call refers to a particular nucleotide identification (e.g., dATP ("A"), dCTP ("C"), dGTP ("G"), or dTTP ("T")). Base calling may include performing one or more signal normalizations, signal phase and signal decay (e.g, enzyme efficiency loss) estimations, and signal corrections, and may identify or estimate base calls for each flow for each defined space. Any suitable base calling method may be used. Preferably, base calling may be performed as described in Davey et al., U.S. Pat. Appl. Publ. No. 2012/0109598, published on May 3, 2012, and/or Sikora et al., U.S. Pat. Appl. Publ. No. 2013/0060482, published on Mar. 7, 2012.

Figure 5:
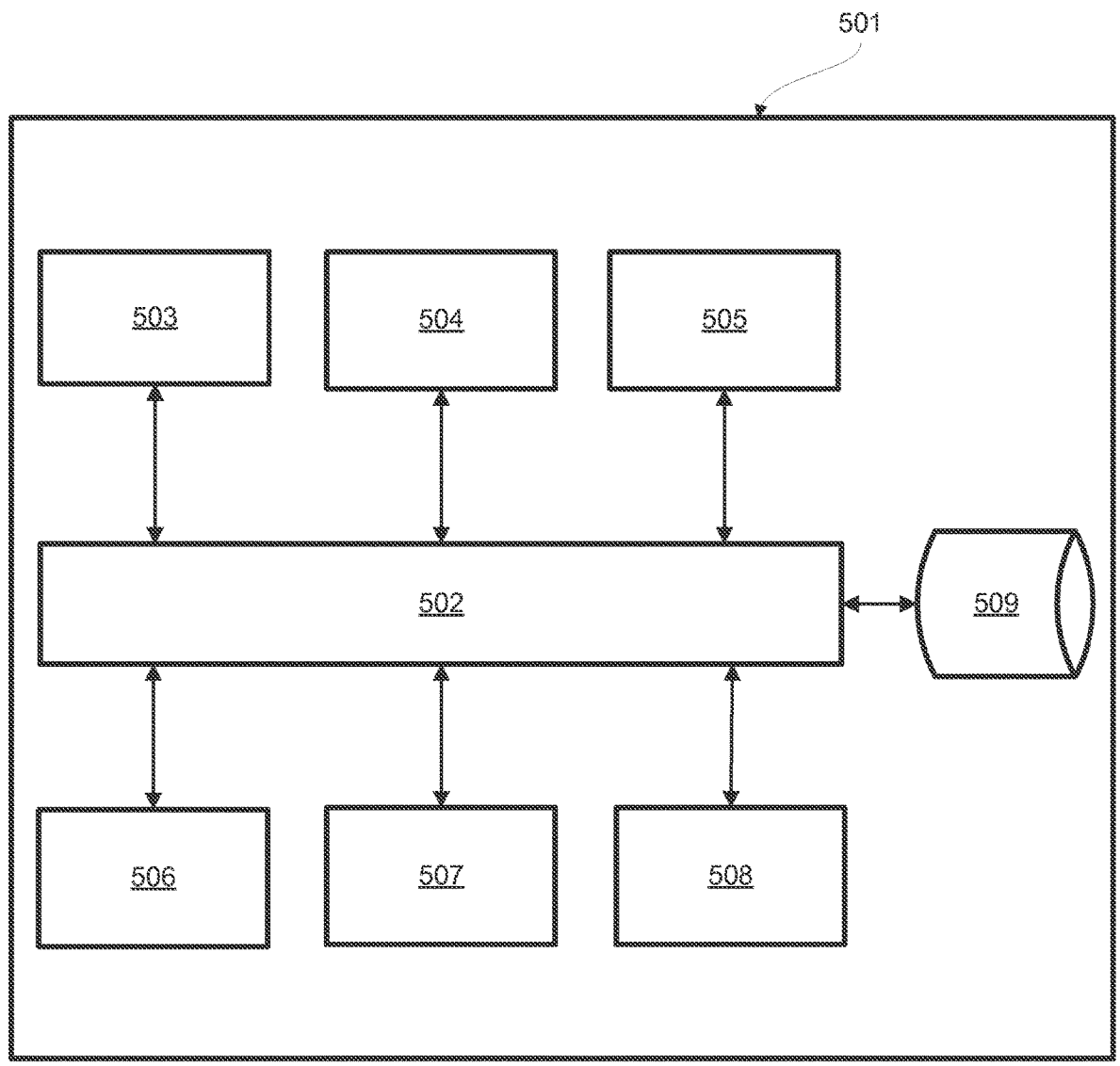
FIG. 5 illustrates an exemplary computer system.

FIG. 5 illustrates an exemplary computer system. The computer system 501 includes a bus 502 or other communication mechanism for communicating information, a processor 503 coupled to the bus 502 for processing information, and a memory 505 coupled to the bus 502 for dynamically and/or statically storing information. The computer system 501 can also include one or more co-processors 504 coupled to the bus 502, such as GPUs and/or FPGAs, for performing specialized processing tasks; a display 506 coupled to the bus 502, such as a cathode ray tube (CRT) or liquid crystal display (LCD), for displaying information to a computer user; an input device 507 coupled to the bus 502, such as a keyboard including alphanumeric and other keys, for communicating information and command selections to the processor 503; a cursor control device 508 coupled to the bus 502, such as a mouse, a trackball or cursor direction keys for communicating direction information and command selections to the processor 503 and for controlling cursor movement on display 506; and one or more storage devices 509 coupled to the bus 502, such as a magnetic disk or an optical disk, for storing information and instructions. The memory 505 may include a random access memory (RAM) or other dynamic storage device and/or a read only memory (ROM) or other static storage device. Such an exemplary computer system with suitable software may be used to perform the embodiments described herein.

More generally, in various embodiments, one or more features of the teachings and/or embodiments described herein may be performed or implemented using appropriately configured and/or programmed hardware and/or software elements.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various embodiments, one or more features of teachings and/or embodiments described herein may be performed or implemented using appropriately configured and/or programmed non-transitory machine-readable medium or article that may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and nonvolatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various embodiments, one or more features of the teachings and/or embodiments described herein may be performed or implemented at least partly using a distributed, clustered, remote, or cloud computing resource.

Figure 6:
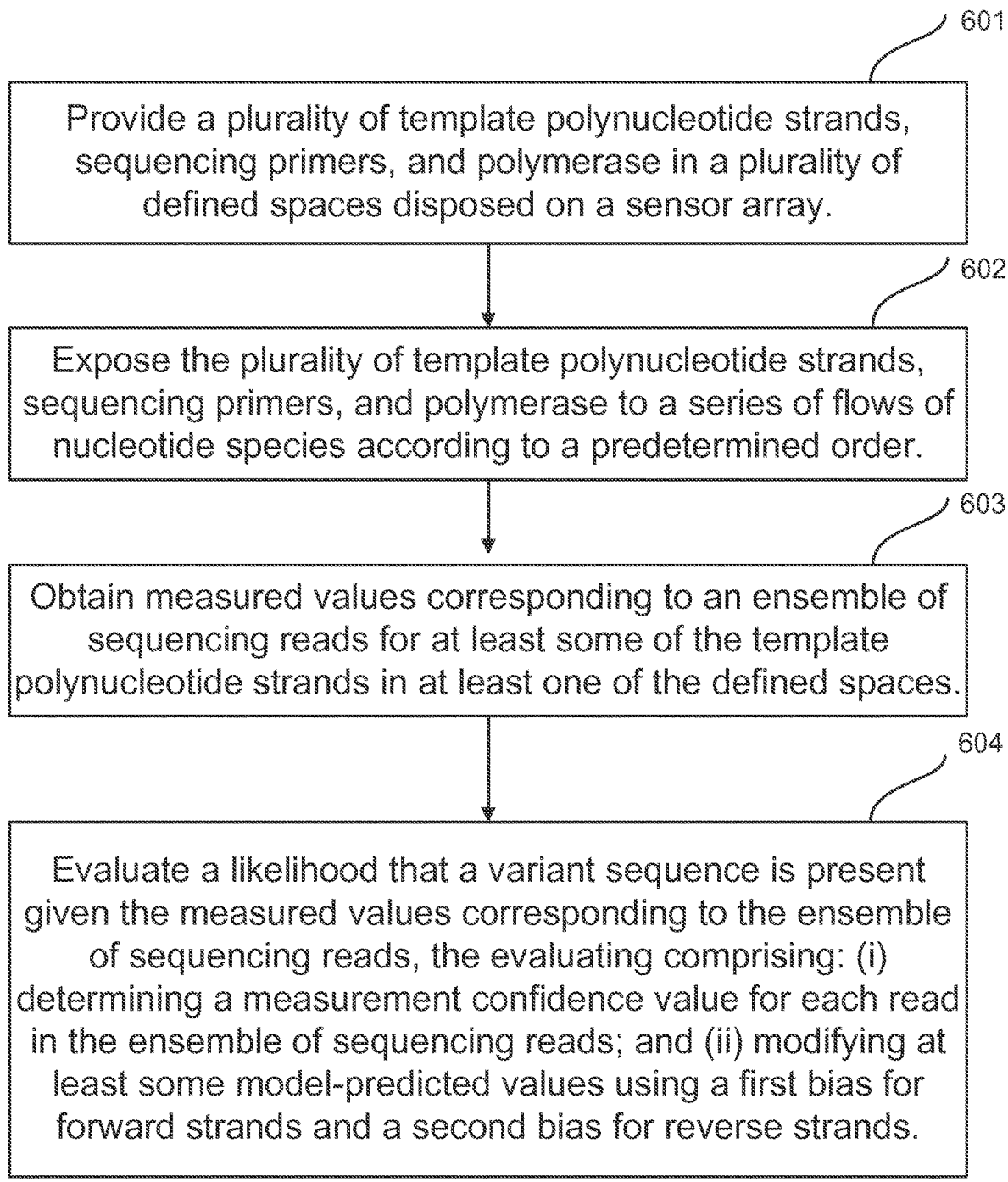
FIG. 6 illustrates an exemplary method for evaluating variant likelihood.

FIG. 6 illustrates an exemplary method for evaluating variant likelihood. In step 601, a user or component provides a plurality of template polynucleotide strands, sequencing primers, and polymerase in a plurality of defined spaces disposed on a sensor array. In step 602, a user or component exposes the plurality of template polynucleotide strands, sequencing primers, and polymerase to a series of flows of nucleotide species according to a predetermined order. In step 603, a server or other computing means or resource obtains measured values corresponding to an ensemble of sequencing reads for at least some of the template polynucleotide strands in at least one of the defined spaces. The measured values may include voltage data indicative of hydrogen ion concentrations, which may be processed and analyzed to yield sequences of base calls for the reads, which may in turn be aligned and mapped. In step 604, the server or other computing means or resource evaluates a likelihood that a variant sequence is present given the measured values corresponding to the ensemble of sequencing reads, the evaluating comprising: (i) determining a measurement confidence value for each read in the ensemble of sequencing reads; and (ii) modifying at least some model-predicted values using a first bias for forward strands and a second bias for reverse strands.

Figure 7A:
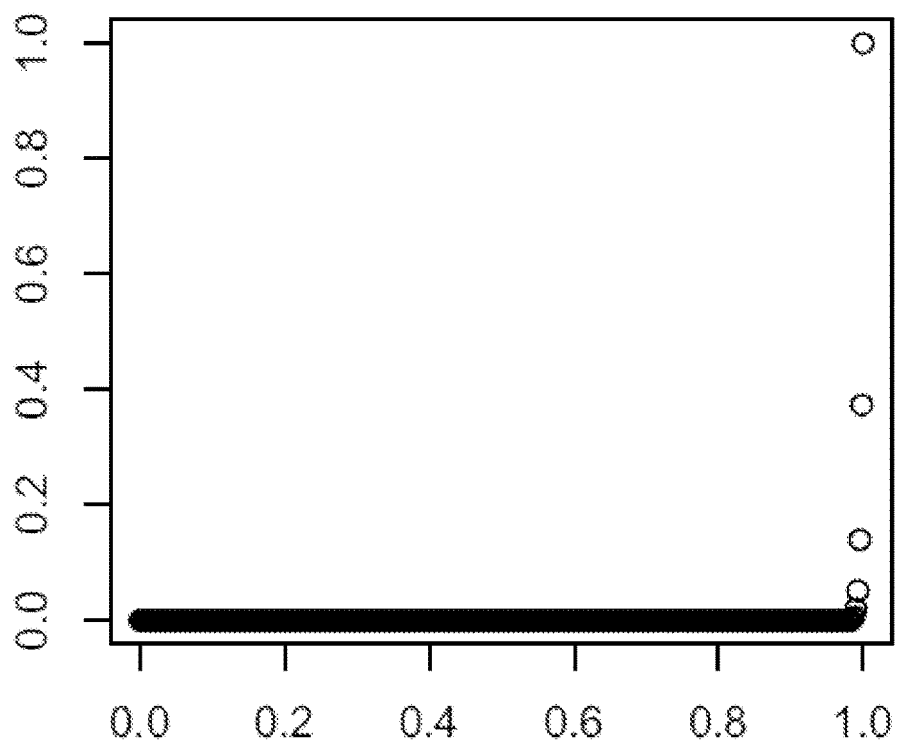
FIG. 7A illustrates an exemplary plot of sample frequency.

FIG. 7A illustrates an exemplary plot of sample frequency. The y-axis shows the posterior density of the sample frequency π conditional on the other values after the maximization algorithm has converged. The x-axis shows the major frequency. The density is derived from maximization of the ensemble likelihood of all reads as described herein by estimating π, $\rho_i$, $\sigma_{ij}^2$, and the two biases. The density is scaled so that the maximum likelihood is 1.0 (which occurs at 100% frequency of the variant allele).

Figure 7B:
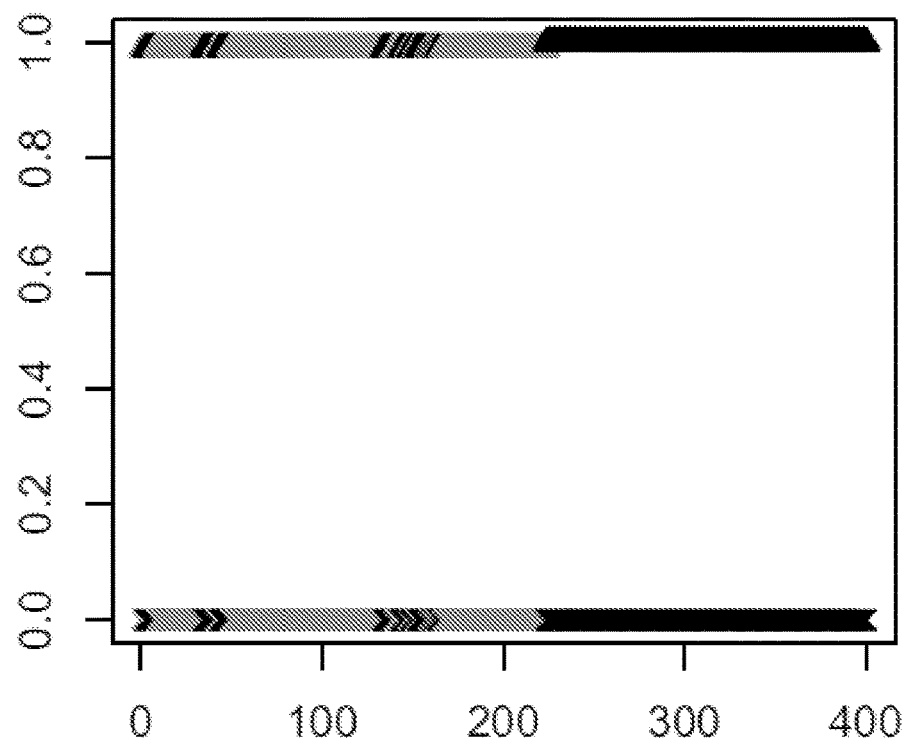
FIG. 7B illustrates an exemplary plot of responsibility for each read.

FIG. 7B illustrates an exemplary plot of responsibility for each read. The y-axis shows the responsibility $p_i$ for each read, calculated at the maximum likelihood estimate for the sample frequency. The x-axis show integers corresponding to the reads. Two data points are plotted per read—one is the responsibility for reference (triangle, near 100%), and one is the responsibility for variant allele (cross, near 0%). (Not shown is the outlier case, which makes these two responsibilities not quite add to 1.0.) The strand for the read is indicated by gray (reverse) or black (forward).

Figure 8A:
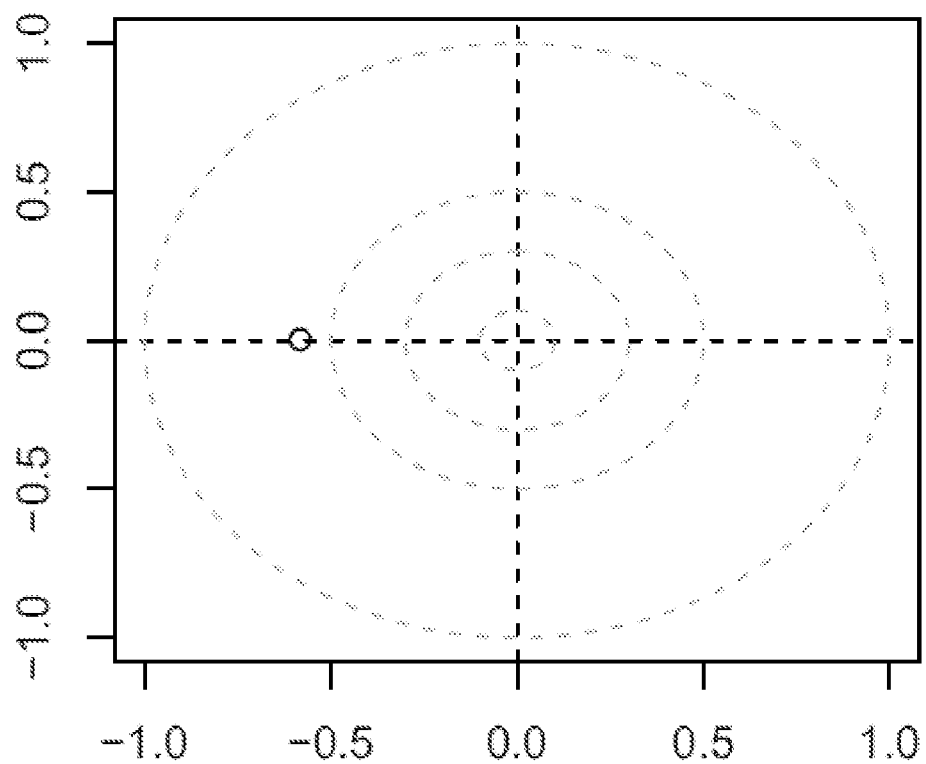
FIG. 8A illustrates exemplary bias terms for each strand for an ensemble of reads.

FIG. 8A illustrates exemplary bias terms for each strand for an ensemble of reads. The graph shows the computed bias terms for each strand for the ensemble of reads. The y-axis shows the reverse bias. The x-axis shows the forward bias. In this case, there is exactly one point, indicating that when the procedure has converged on this set of reads for this variant, the estimate of bias on the forward strand is approximately –0.5 and the estimate of bias on the reverse strand is close to 0. This ensemble bias may then be applied per read per flow as discussed above.

Figure 8B:
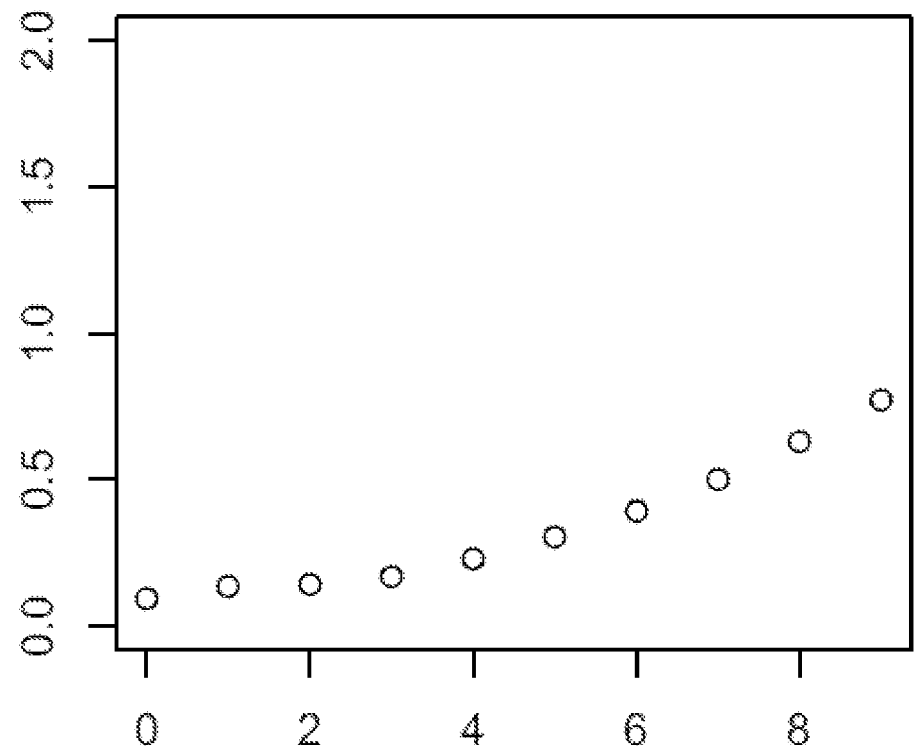
FIG. 8B illustrates exemplary variance components corresponding to homopolymers.

FIG. 8B illustrates exemplary variance components corresponding to homopolymers. The y-axis shows the standard deviation (square root of the variance) for the variance components fitted by the model and used to estimate the variance for each flow in each read by interpolation. The x-axis shows intensities corresponding to homopolymers scaled so that a completely in-phase 1-mer should read 1.0. (When there is insufficient data, the graph shows the prior estimate for this estimate of variation.)

Figure 9A:
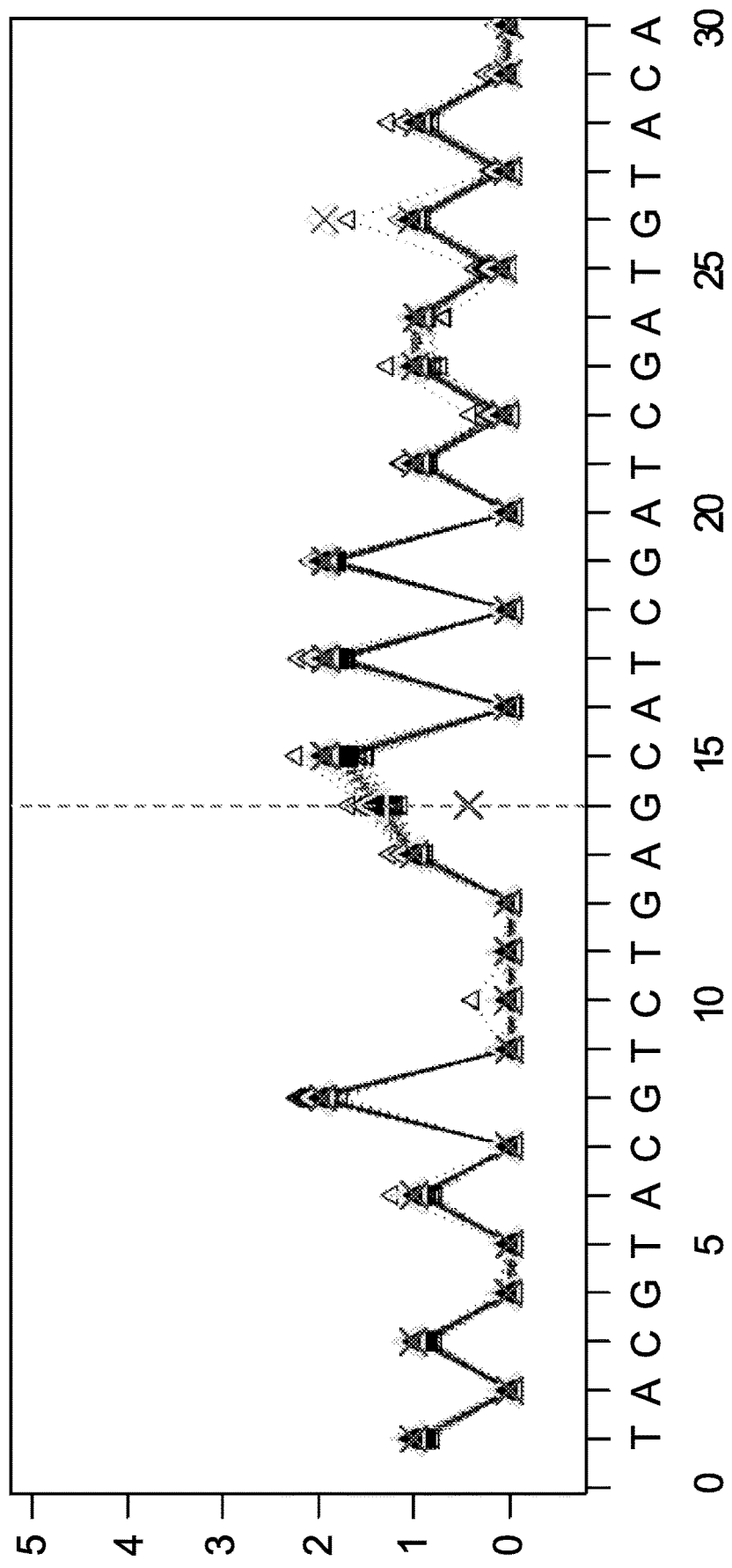
FIG. 9A illustrates predicted/measured data ratios for a sequence of nucleotide flows. Figure discloses SEQ ID NO: 1.

FIG. 9A illustrates predicted/measured data ratios for a sequence of nucleotide flows. The y-axis shows the predicted/measured signal ratio for reads on the forward strand (in black). The x-axis shows a series of nucleotide flows as discussed herein (e.g., a flow of dTTP, followed by a flow of dATP, followed by a flow of dCTP, etc.). The y-axis values are normalized based on the first flows corresponding to a key (see T, C, and A at flows 1, 3, and 6 with the final G of the key combining with the G in the read to form a 2-mer G at flow 8) so that the key values are at 1.0. There is a 1-mer A at flow 13 and a 2-mer C at flow 15. At flow 14 there should be a 2-mer G, however, the value is about half-way between a 1-mer and a 2-mer. At such an early position in the read there should not be "phase" effects reducing the signal. Further, this can be observed across many reads at the same sequence position (and flow) and may thus not be due to noise in any one well. Modified predictions for the reference sequence are shown in cyan triangles; predictions for the intensity that would be observed if the true underlying sequence for reads were a deleted G are shown as blue crosses. As can be observed, the modified predictions fit the measurements quite well.

Figure 9B:
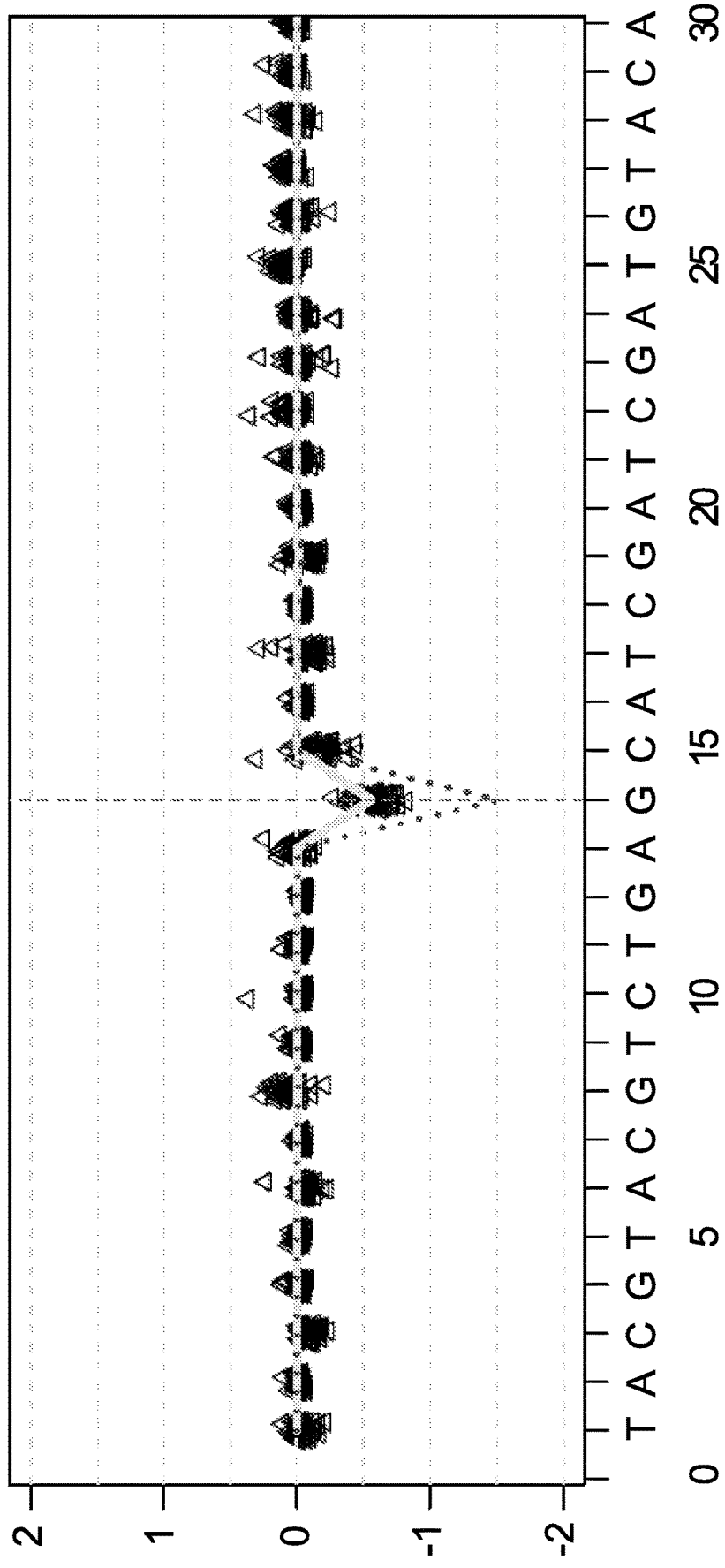
FIG. 9B illustrates residual values for the same data as in FIG. 9A. Figure discloses SEQ ID NO: 1.

FIG. 9B illustrates residual values for the same data as in FIG. 9A. The y-axis shows the residuals $\delta_{ij}$ representing differences between measured and predicted values. The x-axis shows a series of nucleotide flows as discussed herein. The middle line, with a value of 0, means that the model applied to the reference sequence would predict the intensity correctly. Dots placed off the middle line indicate the measurement-prediction difference is large in the original system. The corrected predictions are indicated by the cyan line for reference (passing through the middle of the residuals); the dotted blue line shows the predictions for the variant allele (deleted G). This strand has a bias on the positive strand of –0.58—nearly 60% of a 1-mer. It is therefore unsurprising that this strand is reporting deletion alleles.

Figure 9C:
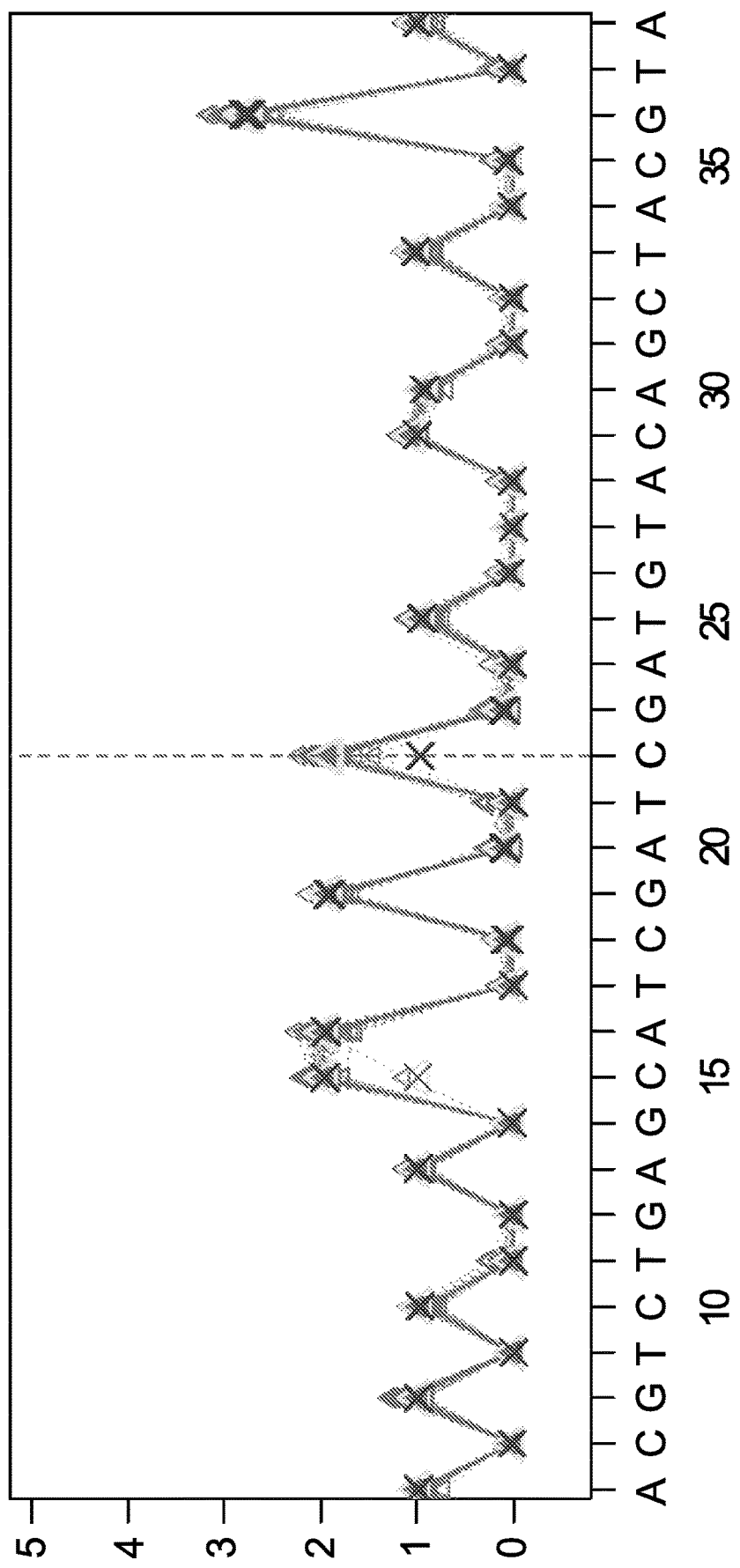
FIG. 9C illustrates predicted/measured data ratios for a sequence of nucleotide flows. Figure discloses SEQ ID NO: 2.

FIG. 9C illustrates predicted/measured data ratios for a sequence of nucleotide flows. The y-axis shows the predicted/measured signal ratio for reads overlapping the same sequence portion as in FIG. 9A but on the reverse strand (in red). The x-axis shows a series of nucleotide flows as discussed herein (e.g., a flow of dATP, followed by a flow of dCTP, followed by a flow of dGTP, etc.). On this strand, the 2-mer C in flow 22 (corresponding to the G on the forward strand in flow 14) has a similar signal to the 2-mer G in flow 19 (corresponding to the C on the forward strand in flow 15). Modified predictions for the reference sequence are shown in cyan triangles; predictions for the intensity that would be observed if the true underlying sequence for reads were a deleted G are shown as blue crosses.

Figure 9D:
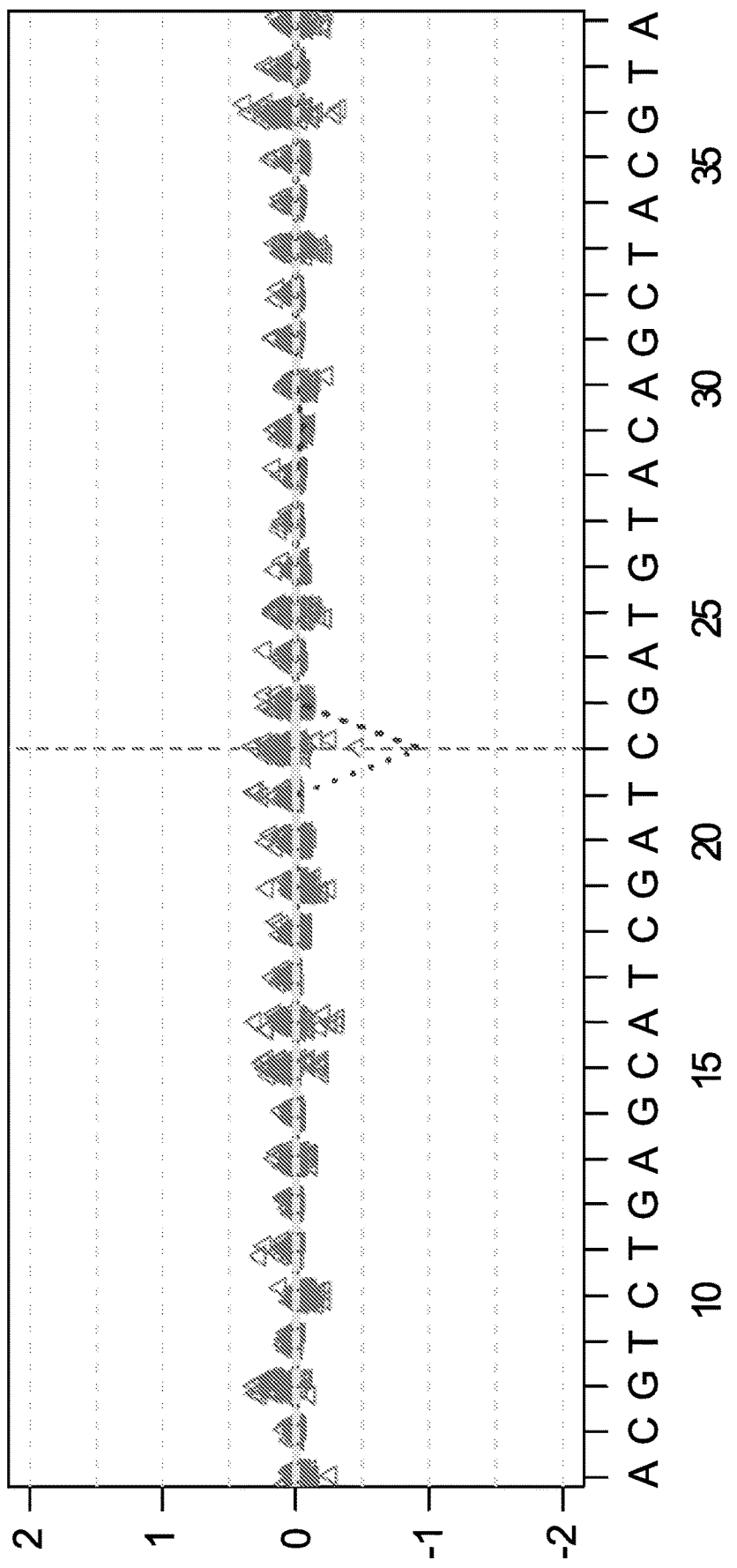
FIG. 9D illustrates residual values for the same data as in FIG. 9C. Figure discloses SEQ ID NO: 2.

FIG. 9D illustrates residual values for the same data as in FIG. 9C. The y-axis shows the residuals $\delta_{ij}$ representing differences between measured and predicted values. The x-axis shows a series of nucleotide flows as discussed herein. Here, the modified prediction line (blue) for reference lies along the horizontal axis, indicating that the predictions are on average centered around the reference value. Unsurprisingly, there are no deletion alleles originally called on this strand.

According to an exemplary embodiment, there is provided a method for evaluating variant likelihood in nucleic acid sequencing, comprising: (a) providing a plurality of template polynucleotide strands, sequencing primers, and polymerase in a plurality of defined spaces disposed on a sensor array; (b) exposing the plurality of template polynucleotide strands, sequencing primers, and polymerase to a series of flows of nucleotide species according to a predetermined order; (c) obtaining measured values corresponding to an ensemble of sequencing reads for at least some of the template polynucleotide strands in at least one of the defined spaces; and (d) evaluating a likelihood that a variant sequence is present given the measured values corresponding to the ensemble of sequencing reads, the evaluating comprising: determining a measurement confidence value for each read in the ensemble of sequencing reads, wherein the determining is based on variations between the measured values and model-predicted values for hypothesized sequences obtained using the predictive model of nucleotide incorporations responsive to flows of nucleotide species.

According to an exemplary embodiment, there is provided a method for evaluating variant likelihood in nucleic acid sequencing, comprising: (a) providing a plurality of template polynucleotide strands, sequencing primers, and polymerase in a plurality of defined spaces disposed on a sensor array; (b) exposing the plurality of template polynucleotide strands, sequencing primers, and polymerase to a series of flows of nucleotide species according to a predetermined order; (c) obtaining measured values corresponding to an ensemble of sequencing reads for at least some of the template polynucleotide strands in at least one of the defined spaces; and (d) evaluating a likelihood that a variant sequence is present given the measured values corresponding to the ensemble of sequencing reads, the evaluating comprising: (i) determining a measurement confidence value for each read in the ensemble of sequencing reads; and (ii) modifying at least some model-predicted values using a first bias for forward strands and a second bias for reverse strands.

According to an exemplary embodiment, there is provided a method for evaluating variant likelihood in nucleic acid sequencing, comprising: (a) providing a plurality of template polynucleotide strands, sequencing primers, and polymerase in a plurality of defined spaces disposed on a sensor array; (b) exposing the plurality of template polynucleotide strands, sequencing primers, and polymerase to a series of flows of nucleotide species according to a predetermined order; (c) obtaining measured values corresponding to an ensemble of sequencing reads for at least some of the template polynucleotide strands in at least one of the defined spaces; and (d) evaluating a likelihood that a variant sequence is present given the measured values corresponding to the ensemble of sequencing reads, the evaluating comprising: (i) determining a measurement confidence value for each read in the ensemble of sequencing reads, wherein the determining is based on variations between the measured values and model-predicted values for hypothesized sequences obtained using a predictive model of nucleotide incorporations responsive to flows of nucleotide species; and (ii) modifying at least some model-predicted values using a first bias for forward strands and a second bias for reverse strands, wherein the modifying is based on variations between model-predicted values for different hypothesized sequences obtained using the predictive model of nucleotide incorporations responsive to flows of nucleotide species.

In such a method, modifying the at least some model-predicted values may comprise applying a transformation including a product of (i) one of the first and second biases and (ii) a discriminant vector representing a difference between model-predicted values corresponding to different hypothesized sequences.

In such a method, modifying the at least some model-predicted values may comprise applying a transformation $q_j^x = p_j^x + \beta_f * d_j$ for forward strands and a transformation $q_j^x = p_j^x + \beta_r * d_j$ for reverse strands, where: $q_j^x$ represents modified model-predicted values for a given sequencing read at flow j under hypothesized sequence x; $p_f$ denotes the first bias for forward strands; $\beta_r$ denotes the second bias for reverse strands; $d_j = p_j^x - p_j^y$ represents a discriminant vector for the given sequencing read; $p_j^x$ and $p_j^y$ represent predicted values for the given sequencing read at flow j under hypothesized sequences x and y, respectively; j is an integer between 1 and M; and M represents a number of flows.

In such a method, evaluating the likelihood may further comprise assigning a first frequency to a variant sequence and a second frequency to a non-variant sequence, and calculating a likelihood of having observed the ensemble of sequencing reads conditioned on the first frequency as a function of a product of the likelihoods of having observed each of the sequencing reads given the first frequency. The likelihood of having observed the ensemble of sequencing reads may be determined using an expression comprising:

$$P(\pi) * \prod_{i=1}^{N} (\pi * \epsilon_i + (1-\pi) * (1-\epsilon_i))$$

where: $\pi$ represents the first frequency; $1-\pi$ represents the second frequency; $P(\pi)$ represents a prior probability of $\pi$; $\epsilon_1$ represents the measurement confidence value for sequencing read i; i is an integer between 1 and N identifying a sequencing read; and N is an integer specifying a number of sequencing reads in the ensemble.

In such a method, evaluating the likelihood may further comprise assigning a first frequency to a variant sequence, a second frequency to a non-variant sequence, and a third frequency to an outlier event. The outlier event may have a flat density across all sequencing reads in the ensemble. Evaluating the likelihood may further comprise calculating a likelihood of having observed the ensemble of sequencing reads conditioned on the third frequency as a function of a product of the likelihoods of having observed each of the sequencing reads given the third frequency. The likelihood of having observed the ensemble of sequencing reads may be determined using an expression comprising $$P(\pi) * \prod_{i=1}^{N} (\tau * (\pi * \epsilon_i + (1-\pi) * (1-\epsilon_i)) + (1-\tau) * T)$$

where: $\pi$ represents the first frequency; $1-\pi$ represents the second frequency; $(1-\tau)$ represents the third frequency; T represents a density of the outlier event; $P(\pi)$ represents a prior probability of $\pi$; $\epsilon_i$ represents a measurement confidence value for sequencing read i; i is an integer between 1 and N identifying a sequencing read; and N is an integer specifying a number of sequencing reads in the ensemble.

In such a method, the measurement confidence values may be estimated using a function comprising a sum of log-likelihood of values measured for a given flow given a hypothesized sequence. The measurement confidence values may further be estimated using a function comprising differences between the measured values and the model-predicted values. The differences between measured and model-predicted values at each nucleotide flow may be assumed to follow independent normal distributions each having a mean and a variance. The differences between measured and model-predicted values at each nucleotide flow may also be assumed to follow independent t-distributions.

In such a method, the measurement confidence values may be estimated using an expression comprising $$\epsilon_i = \frac{1}{1 + \exp(LL_{yi} - LL_{xi})}$$

where $LL_{yi}$ and $LL_{xi}$ are log-likelihoods of values measured for a given sequencing read under hypothesized sequences y and x, respectively. The log-likelihoods of values measured for a given sequencing read under hypothesized sequences y and x may be expressed as $$LL_{xi} = \sum_{j=1}^{M} \left( -\ln(\sigma_{ij}^x) + \frac{(\delta_{ij}^x)^2}{2 * (\sigma_{ij}^x)^2} \right) \text{ and}$$

$$LL_{yi} = \sum_{j=1}^{M} \left( -\ln(\sigma_{ij}^y) + \frac{(\delta_{ij}^y)^2}{2 * (\sigma_{ij}^y)^2} \right)$$

where $\delta_{ij}^x = m_{ij}^x - p_{ij}^x$ and $\delta_{ij}^y = m_{ij}^y - p_{ij}^y$, where $m_{ij}^x$ and $m_{ij}^y$ represent measured values for read i at flow j under hypothesized sequences x and y, respectively, where $\sigma_{ij}^x$ and $\sigma_{ij}^y$ represent predicted values for read i at flow j under hypothesized sequences x and y, respectively, where $\sigma_{ij}^x$ and $\sigma_{ij}^y$ are the standard deviations of independently distributed normal distributions for read i at flow j under hypothesized sequences x and y, respectively, where i is an integer identifying a sequencing read, and where M represents a number of flows.

In such a method, the measurement confidence values may be estimated using an expression for responsibility comprising $$\rho_i = \frac{\pi}{\pi + (1-\pi)*\exp(LL_{yi} - LL_{xi})}$$

where $\pi$ represents a first frequency assigned to a variant sequence, $1-\pi$ represents a second frequency assigned to a non-variant sequence, and $\rho_i$ represents a measure of responsibility for each of the sequencing reads in the ensemble. In the responsibility framework, the variance may then be estimated using an expression comprising $$\hat{\sigma}^2 = \frac{\sum_{i=1}^{N}\left(\rho_i \sum_{j=1}^{M}(\delta_{ij}^x)^2 + (1-\rho_i)\sum_{j=1}^{M}(\delta_{ij}^y)^2\right)}{N}$$

where $\delta_{ij}^x = m_{ij}^x - p_{ij}^x$ and $\delta_{ij}^y = m_{ij}^y - p_{ij}^y$, where $m_{ij}^x$ and $m_{ij}^y$ represent measured values for read i at flow j under hypothesized sequences x and y, respectively, where $p_{ij}^x$ and $p_{ij}^y$ represent predicted values for read i at flow j hypothesized sequences x and y, respectively, where M represents a number of flows and N is an integer specifying a number of sequencing reads, and where $$\rho_i = \frac{\pi}{\pi + (1-\pi)*\exp(LL_{yi} - LL_{xi})}$$

and $$LL_{xi} = \sum_{j=1}^{M}\left(-\ln(\sigma_{ij}^x) + \frac{(\delta_{ij}^x)^2}{2*(\sigma_{ij}^x)^2}\right) \text{ and}$$

$$LL_{yi} = \sum_{j=1}^{M}\left(-\ln(\sigma_{ij}^y) + \frac{(\delta_{ij}^y)^2}{2*(\sigma_{ij}^y)^2}\right).$$

In such a method, the variance may be estimated by decomposition of the variance in a flow and sequencing read into underlying latent components. The decomposition may comprise an expression $\sigma_{ij}^2 = \sum_{m=1}^{K}(\varphi_{ijm}*\sigma_m^2)$ where $\sigma_m^2$ is a latent component and $\varphi_{ijm}$ is a proportionality constant determining an amount of variation contributed by the mth latent component. The method may further comprise updating the decomposition using an expression comprising $$\sigma_{kn}^2 = \frac{\sum(\omega_i * r_{ij}^2)}{\sum(\varphi_{ijm})}$$

where $$\omega_{ij} = \frac{\varphi_{ijm} * \sigma_{k,n-1}^2}{\sum(\varphi_{ijm} * \sigma_{m,n-1}^2)}$$

for the k-th component using the proportion of variance attributed to each flow. In some cases, each latent component may correspond to a homopolymer having an integer length. In another case, the latent components may include a null variance component representing contribution to a flow regardless of any nucleotide incorporation, a residual variance component representing contribution for nucleotide incorporations not explicitly modeled, and one or more additional variance components. The one or more additional variance components may comprise variance components associated with homopolymers having an integer length. In some cases, the latent components may be estimated using an EM methodology and a method of moments approximation.

In such a method, evaluating the likelihood may comprise estimating (i) a first frequency $\pi$ assigned to a variant sequence, (ii) at least one of a measurement confidence value $\epsilon_i$ for each of the sequencing reads in the ensemble and a measure of responsibility $\rho_i$ for each of the sequencing reads in the ensemble, and (iii) a variance $\sigma_{ij}^2$ for each of the flows and sequencing reads in the ensemble. Evaluating the likelihood may further comprise estimating $\pi$, $\epsilon_1$ (or $\rho_i$), and $\sigma_{ij}^2$ individually conditional on the values of the others.

According to an exemplary embodiment, there is provided a non-transitory machine-readable storage medium comprising instructions which, when executed by a processor, cause the processor to perform a method for evaluating variant likelihood in nucleic acid sequencing comprising: (a) obtaining measured values corresponding to an ensemble of sequencing reads for at least some template polynucleotide strands in at least one defined space, wherein a plurality of template polynucleotide strands, sequencing primers, and polymerase have been provided in a plurality of defined spaces disposed on a sensor array, and wherein the plurality of template polynucleotide strands, sequencing primers, and polymerase have been exposed to a series of flows of nucleotide species according to a predetermined order; and (b) evaluating a likelihood that a variant sequence is present given the measured values corresponding to the ensemble of sequencing reads, the evaluating comprising: (i) determining a measurement confidence value for each read in the ensemble of sequencing reads, wherein the determining is based on variations between the measured values and model-predicted values for hypothesized sequences obtained using a predictive model of nucleotide incorporations responsive to flows of nucleotide species; and (ii) modifying at least some model-predicted values using a first bias for forward strands and a second bias for reverse strands, wherein the modifying is based on variations between model-predicted values for different hypothesized sequences obtained using the predictive model of nucleotide incorporations responsive to flows of nucleotide species.

According to an exemplary embodiment, there is provided a system for evaluating variant likelihood in nucleic acid sequencing, including: a plurality of template polynucleotide strands, sequencing primers, and polymerase provided in a plurality of defined spaces disposed on a sensor array; an apparatus configured to expose the plurality of template polynucleotide strands, sequencing primers, and polymerase to a series of flows of nucleotide species according to a predetermined order; a machine-readable memory; and a processor configured to execute machine-readable instructions, which, when executed by the processor, cause the system to perform a method for evaluating variant likelihood, comprising: (a) obtaining measured values corresponding to an ensemble of sequencing reads for at least some of the template polynucleotide strands in at least one of the defined spaces; and (b) evaluating a likelihood that a variant sequence is present given the measured values corresponding to the ensemble of sequencing reads, the evaluating comprising: (i) determining a measurement confidence value for each read in the ensemble of sequencing reads, wherein the determining is based on variations between the measured values and model-predicted values for hypothesized sequences obtained using a predictive model of nucleotide incorporations responsive to flows of nucleotide species; and (ii) modifying at least some model-predicted values using a first bias for forward strands and a second bias for reverse strands, wherein the modifying is based on variations between model-predicted values for different hypothesized sequences obtained using the predictive model of nucleotide incorporations responsive to flows of nucleotide species.

Unless otherwise specifically designated herein, terms, techniques, and symbols of biochemistry, cell biology, genetics, molecular biology, nucleic acid chemistry, nucleic acid sequencing, and organic chemistry used herein follow those of standard treatises and texts in the relevant field.

Although the present description described in detail certain embodiments, other embodiments are also possible and within the scope of the present invention. For example, those skilled in the art may appreciate from the present description that the present teachings may be implemented in a variety of forms, and that the various embodiments may be implemented alone or in combination. Variations and modifications will be apparent to those skilled in the art from consideration of the specification and figures and practice of the teachings described in the specification and figures, and the claims.

sequencing primers, and polymerase are disposed in a plurality of microwells of a microwell array aligned with a corresponding plurality of sensors of a sensor array, wherein the plurality of microwells is at least $10^5$ microwells;

measuring, using the sensor array, electrical or chemical changes in the plurality of microwells resulting from incorporation of the nucleotide species into the plurality of primer extensions to obtain an ensemble of sequencing reads corresponding to the plurality of primer extensions;

converting the electrical or chemical changes measured using the sensor array into output signals;

assigning measured values, based on the output signals, to the ensemble of sequencing reads;

calculating model-predicted values for the plurality of template polynucleotide strands utilizing a predictive model of nucleotide incorporations resulting from flows of nucleotide species according to the predetermined order;

modifying at least some model-predicted values using a first bias for forward strands and a second bias for reverse strands, wherein the modifying is based on variations between model-predicted values for different hypothesized sequences obtained using the predictive model of nucleotide incorporations resulting from the flows of nucleotide species according to the predetermined order;

calculating a measurement confidence value for each read in the ensemble of sequencing reads, wherein the confidence value represents variations between the

The invention claimed is:

1. A method of identifying sequence variants, the method comprising:
exposing a plurality of template polynucleotide strands, sequencing primers, and polymerase to a series of flows of nucleotide species according to a predetermined order to form a plurality of primer extensions, wherein the plurality of template polynucleotide strands, measured values and the modified model-predicted values; and
identifying a plurality of reads in the ensemble as corresponding to a variant sequence based on the measurement confidence value.

2. The method of claim 1, wherein the modifying comprises applying a transformation including a product of one of the first bias and the second bias and a discriminant vector representing a difference between vectors of model-predicted values corresponding to different hypothesized sequences.

3. The method of claim 1, further comprising:
assigning a first frequency to the variant sequence;
assigning a second frequency to a non-variant sequence; and
calculating a likelihood of observing each of the variant sequence and the non-variant sequence in the ensemble of sequencing reads based on the first and second frequencies.

4. The method of claim 3, further comprising assigning a third frequency to an outlier event, wherein the outlier event is an event in which a sequence other than the variant sequence and the non-variant sequence occurs.

5. The method of claim 4, wherein the outlier event has a flat density across all sequencing reads in the ensemble.

6. The method of claim 4, wherein the calculating the likelihood further comprises calculating the likelihood of observing an outlier event in the ensemble based further on the third frequency.

7. The method of claim 1, wherein the measurement confidence values are estimated using a function comprising a sum of a log of the likelihood of values measured for a given flow given a hypothesized sequence of the different hypothesized sequences.

8. The method of claim 7, wherein the measurement confidence values are calculated using a function comprising differences between the measured values and the model-predicted values.

9. The method of claim 8, wherein the differences between measured and model-predicted values at each nucleotide flow are modeled to follow independent normal distributions each having a mean and a variance.

10. The method of claim 9, wherein the differences between measured and model-predicted values at each nucleotide flow are modeled to follow independent t-distributions.

11. The method of claim 9, wherein the variance is estimated by decomposition of the variance in a flow and sequencing read into underlying latent components.

12. The method of claim 11, wherein each latent component corresponds to a homopolymer having an integer length.

13. The method of claim 11, wherein the latent components include a null variance component representing contribution to a flow regardless of any nucleotide incorporation, a residual variance component representing contribution for nucleotide incorporations not explicitly modeled, and one or more additional variance components.

14. The method of claim 13, wherein the one or more additional variance components comprise variance components associated with homopolymers having an integer length.

15. The method of claim 11, wherein the latent components are estimated using an expectation-maximization (EM) methodology and a method of moments approximation.

16. The method of claim 1, wherein the measurement confidence values are calculated using an expression comprising $$\epsilon_i = \frac{1}{1 + \exp(LL_{yi} - LL_{xi})}$$

where $LL_{yi}$ and $LL_{xi}$ are log-likelihoods of values measured for a given sequencing read under hypothesized sequences y and x, respectively.

17. The method of claim 16, wherein the measurement confidence values are calculated using an expression for responsibility comprising $$\rho_i = \frac{\pi}{\pi + (1 - \pi) * \exp(LL_{yi} - LL_{xi})}$$

where $\pi$ represents a first frequency assigned to a variant sequence, $1-\pi$ represents a second frequency assigned to a non-variant sequence, and $\rho_i$ represents a measure of responsibility for each of the sequencing reads in the ensemble.

18. The method of claim 1, further comprising estimating (i) a first frequency $\pi$ assigned to a variant sequence, (ii) at least one of a measurement confidence value $\epsilon_i$ for each of the sequencing reads in the ensemble and a measure of responsibility $\rho_i$ for each of the sequencing reads in the ensemble, and (iii) a variance $\sigma_{ij}^2$ for each of the flows and sequencing reads in the ensemble.

19. A non-transitory machine-readable storage medium comprising instructions which, when executed by a processor, to cause the processor to perform a method comprising:
exposing a plurality of template polynucleotide strands, sequencing primers, and polymerase to a series of flows of nucleotide species according to a predetermined order to form a plurality of primer extensions, wherein the plurality of template polynucleotide strands, sequencing primers, and polymerase are disposed in a plurality of microwells of a microwell array aligned with a corresponding plurality of sensors of a sensor array, wherein the plurality of microwells is at least $10^5$ microwells;
measuring, using the sensor array, electrical or chemical changes in the plurality of microwells resulting from incorporation of the nucleotide species into the plurality of primer extensions to obtain an ensemble of sequencing reads corresponding to the plurality of primer extensions;
converting the electrical or chemical changes measured using the sensor array into output signals;
assigning measured values, based on the output signals, to the ensemble of sequencing reads;
calculating model-predicted values for the plurality of template polynucleotide strands utilizing a predictive model of nucleotide incorporations resulting from flows of nucleotide species according to the predetermined order;
modifying at least some model-predicted values using a first bias for forward strands and a second bias for reverse strands, wherein the modifying is based on variations between model-predicted values for different hypothesized sequences obtained using the predictive model of nucleotide incorporations resulting from the flows of nucleotide species according to the predetermined order;
calculating a measurement confidence value for each read in the ensemble of sequencing reads, wherein the confidence value represents variations between the measured values and the modified model-predicted values; and
identifying a plurality of the reads in the ensemble as corresponding to a variant sequence based on the measurement confidence value.

20. A system for identifying sequence variants, including:
a microwell array comprising a plurality of microwells comprising a plurality of template polynucleotide strands, sequencing primers, and polymerase;
a sensor array comprising a plurality of sensors aligned with the plurality of microwells, wherein the plurality of microwells is at least $10^5$ microwells;
a machine-readable memory operably coupled to the sensor array; and
a processor operably coupled to the sensor array and the machine-readable memory, the processor being configured to execute machine-readable instructions, which, when executed by the processor, causes the system to perform a method for improving sensor array accuracy in identifying sequence variants, the method comprising:
exposing the plurality of template polynucleotide strands, the sequencing primers, and the polymerase to a series of flows of nucleotide species according to a predetermined order to form a plurality of primer extensions;
measuring, using the sensor array, electrical or chemical changes in the plurality of microwells resulting from incorporation of the nucleotide species into the plurality of primer extensions to obtain an ensemble of sequencing reads corresponding to the plurality of primer extensions;
converting the electrical or chemical changes measured using the sensor array into output signals;
assigning measured values, based on the output signals, to the ensemble of sequencing reads;
calculating model-predicted values for the plurality of template polynucleotide strands utilizing a predictive model of nucleotide incorporations resulting from flows of nucleotide species according to the predetermined order;
modifying at least some model-predicted values using a first bias for forward strands and a second bias for reverse strands, wherein the modifying is based on variations between model-predicted values for different hypothesized sequences obtained using the predictive model of nucleotide incorporations resulting from the flows of nucleotide species according to the predetermined order;
calculating a measurement confidence value for each read in the ensemble of sequencing reads, wherein the confidence value represents variations between the measured values and the modified model-predicted values; and
identifying a plurality of the reads in the ensemble as corresponding to a variant sequence based on the measurement confidence value.

21. The method of claim 1, wherein the plurality of microwells is at least $10^6$ microwells.

22. The non-transitory machine-readable storage medium of claim 19, wherein the plurality of microwells is at least $10^6$ microwells.

23. The system of claim 20, wherein the plurality of microwells is at least $10^6$ microwells.

* * * * *

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tacgtacgtc tgagcatcga tcgatgtaca                                          30

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acgtctgagc atcgatcgat gtacagctac gta                                      33
```